(12) United States Patent
Sacha et al.

(10) Patent No.: US 10,114,014 B2
(45) Date of Patent: Oct. 30, 2018

(54) MACROMOLECULAR CONJUGATES FOR ISOLATION, IMMOBILIZATION AND VISUALIZATION OF PROTEINS

(71) Applicants: USTAV ORGANICKE CHEMIE A BIOCHEMIE AV CR, V.V.I., Prague (CZ); USTAV MAKROMOLEKULARNI CHEMIE AV CR, V.V.I., Prague-Brevnov (CZ); UNIVERZITA KARLOVA, Prague (CZ)

(72) Inventors: Pavel Sacha, Prague (CZ); Jan Konvalinka, Prague (CZ); Jiri Schimer, Prague (CZ); Tomas Knedlik, Koprivnice (CZ); Vladimir Subr, Melnik (CZ); Karel Ulbrich, Prague (CZ); Jiri Strohalm, Prague (CZ)

(73) Assignees: USTAV ORGANICKE CHEMIE A BIOCHEMIE AV CR, V.V.I., Praha (CZ); USTAV MAKROMOLEKULARNI CHEMIE AV CR, V.V.I., Praha (CZ); UNIVERZITA KARLOVA, Praha (CZ)

( * ) Notice: Subject to any disclaimer, the term of this patent is extended or adjusted under 35 U.S.C. 154(b) by 0 days.

(21) Appl. No.: 15/542,792

(22) PCT Filed: Jan. 13, 2016

(86) PCT No.: PCT/CZ2016/050002
§ 371 (c)(1),
(2) Date: Jul. 11, 2017

(87) PCT Pub. No.: WO2016/112882
PCT Pub. Date: Jul. 21, 2016

(65) Prior Publication Data
US 2018/0011085 A1 Jan. 11, 2018

(30) Foreign Application Priority Data

Jan. 14, 2015 (CZ) .................................. 2015-19

(51) Int. Cl.
*A61K 9/00* (2006.01)
*G01N 33/532* (2006.01)
(Continued)

(52) U.S. Cl.
CPC .............. *G01N 33/532* (2013.01); *C08F 8/30* (2013.01); *G01N 33/531* (2013.01);
(Continued)

(58) Field of Classification Search
CPC .................................................... G01N 33/532
See application file for complete search history.

(56) References Cited

FOREIGN PATENT DOCUMENTS

| CZ | PV2014-527 A3 | 2/2016 |
|---|---|---|
| EP | 0245926 A2 | 11/1987 |

(Continued)

OTHER PUBLICATIONS

Kopecek, "HPMA copolymers: Origins, early developments, present, and future," Advanced Drug Delivery Reviews, 2010, 62(2), 122-149 (Year: 2010).*

(Continued)

*Primary Examiner* — Paul W Dickinson
(74) *Attorney, Agent, or Firm* — Notaro, Michalos & Zaccaria P.C.

(57) ABSTRACT

Synthetic macromolecular conjugate for selective interaction with proteins has a synthetic copolymer, and at least one binding group and at least one further group selected from an affinity tag and an imaging probe, and at least one binding group and at least one further group being bound via covalent bond to the synthetic copolymer. The macromolecular conjugate is suitable in particular for identification, (Continued)

visualization, quantification or isolation of proteins and/or cells.

10 Claims, 9 Drawing Sheets

Specification includes a Sequence Listing.

(51) Int. Cl.
    *G01N 33/531*     (2006.01)
    *G01N 33/533*     (2006.01)
    *G01N 33/534*     (2006.01)
    *C08F 8/30*     (2006.01)
    *G01N 33/58*     (2006.01)

(52) U.S. Cl.
    CPC ......... *G01N 33/533* (2013.01); *G01N 33/534* (2013.01); *G01N 33/58* (2013.01); *G01N 33/582* (2013.01)

(56) References Cited

FOREIGN PATENT DOCUMENTS

| WO | 2004009136 A2 | 1/2004 |
|---|---|---|
| WO | 2005007798 A2 | 1/2005 |

OTHER PUBLICATIONS

Hart, "HPMA copolymer-modified Avidin: Immune Response," Journal of Biomaterials Science, Polymer Edition, 2000, 11, 1-12 (Year: 2000).*

Zarabi, "Macrophage targeted N-(2-hydroxypropyl) methacrylamide conjugates for magnetic resonance imaging," Molecular Pharmaceutics, 2006, 3(5), 550-557 (Year: 2006).*

Tau, "Multifunctional pH-Disintegrable micellar nanoparticles of asymmetrically functionalized-cyclodextrin-based star copolymer covalently conjugated and doxorubicin and DOTA-Gd moieties," Biomaterials, 2012, 33, 2521-2531 (Year: 2012).*

Brandon, "In Vitro Evaluation of HPMA-Copolymers Targeted to HER2 Expressing Pancreatic Tumor Cells for Image Guided Drug Delivery," Macromolecular Bioscience, 2013, 14, 92-99 (Year: 2013).*

Borgman, "Tumor-targeted HPMA copolymer-(RGDfk)-(CHX-A"-DTPA) conjugates show increased kidney accumulation," Journal of Controlled Release, 2008, 132(3), 193-199 (Year: 2008).*

Buckway, "Overcoming the stromal barrier for targeted delivery of HPMA copolymers to pancreatic tumors," International Journal of Pharmaceutics, 2013, 456, 202-211 (Year: 2013).*

Fernandez-Megia, "Conjugation of bioactive ligands to PEG-grafted chitosan at the distal end of PEG," Macromolecules, 2007, 8(3), 833-842 (Year: 2007).*

International Search Report and Written Opinion of corresponding PCT application No. PCT/CZ2016/050002, dated Jan. 13, 2016.

* cited by examiner

A:

B:

SEQUENCE LISTING

```
<160> NUMBER OF SEQ ID NOS: 7

<210> SEQ ID NO 1
<211> LENGTH: 8
<212> TYPE: PRT
<213> ORGANISM: Artificial
<220> FEATURE:
<223> OTHER INFORMATION: FLAG tag

<400> SEQUENCE: 1

Asp Tyr Lys Asp Asp Asp Asp Lys
1               5

<210> SEQ ID NO 2
<211> LENGTH: 9
<212> TYPE: PRT
<213> ORGANISM: Artificial
<220> FEATURE:
<223> OTHER INFORMATION: HA tag

<400> SEQUENCE: 2

Tyr Pro Tyr Asp Val Pro Asp Tyr Ala
1               5

<210> SEQ ID NO 3
<211> LENGTH: 8
<212> TYPE: PRT
<213> ORGANISM: Artificial
<220> FEATURE:
<223> OTHER INFORMATION: Strep-tag

<400> SEQUENCE: 3

Trp Ser His Pro Gln Phe Glu Lys
1               5

<210> SEQ ID NO 4
<211> LENGTH: 10
<212> TYPE: PRT
<213> ORGANISM: Artificial
<220> FEATURE:
<223> OTHER INFORMATION: c-myc-tag

<400> SEQUENCE: 4
```

```
Glu Gln Lys Leu Ile Ser Glu Glu Asp Leu
1               5                   10

<210> SEQ ID NO 5
<211> LENGTH: 14
<212> TYPE: PRT
<213> ORGANISM: Artificial
<220> FEATURE:
<223> OTHER INFORMATION: V5-tag

<400> SEQUENCE: 5

Gly Lys Pro Ile Pro Asn Pro Leu Leu Gly Leu Asp Ser Thr
1               5                   10

<210> SEQ ID NO 6
<211> LENGTH: 13
<212> TYPE: PRT
<213> ORGANISM: Artificial
<220> FEATURE:
<223> OTHER INFORMATION: E-tag

<400> SEQUENCE: 6

Gly Ala Pro Val Pro Tyr Pro Asp Pro Leu Glu Pro Arg
1               5                   10

<210> SEQ ID NO 7
<211> LENGTH: 15
<212> TYPE: PRT
<213> ORGANISM: Artificial
<220> FEATURE:
<223> OTHER INFORMATION: S-tag

<400> SEQUENCE: 7

Lys Glu Thr Ala Ala Ala Lys Phe Glu Arg Gln His Met Asp Ser
1               5                   10                  15
```

MACROMOLECULAR CONJUGATES FOR ISOLATION, IMMOBILIZATION AND VISUALIZATION OF PROTEINS

FIELD OF ART

The present invention describes synthetic macromolecular conjugates allowing isolation, immobilization and visualization of recombinant proteins labeled with a purification tag in biochemistry, molecular biology and related sciences.

BACKGROUND ART

Development of biochemical and molecular-biological methods allowing relatively easy production of large amounts of recombinant proteins in high yields brought the need for their easy and particularly versatile isolation and visualization. Subsequent development of affinity (purification) tags allowed isolation, purification and visualization of various proteins always with the same technology, which meant a significant improvement in methodology of recombinant protein production and acceleration in their isolation and purification.

Polyhistidine sequence (also "tag", abbreviated 6×His-tag), containing usually 6 histidines and known under the commercial name His-tag, is probably the most widely used and best known tag. The 6×His-tag sequence is relatively specifically bound with a complex containing chelating compound with a divalent cation of nickel or cobalt. This chelating compound may be e.g. nitrilotriacetic acid (NTA), which is the most commonly used for purification of proteins tagged with a polyhistidine sequence. Affinity can be further enhanced by using compounds containing more molecules of nitrilotriacetic acid, e.g. triNTA.

For the detection of the proteins with a polyhistidine sequence on Western blot, it is necessary to use antibody recognizing this sequence. The sensitivity of many commercially available antibodies against polyhistidine sequence is not sufficient for the quantification of small amounts of proteins labeled with polyhistidine sequences. The bond between an antibody and a polyhistidine sequence may generally not be strong enough, and thus dissociation of the complex may occur. This is a particular problem in methods requiring a very strong bond to immobilize proteins labeled with polyhistidine sequences, such as ELISA or surface plasmon resonance (SPR).

Glutathione-S-transferase (GST) is a glutathione binding enzyme and is involved in detoxification processes in the organism. GST can be expressed in fusion with the protein (GST-tag); this fusion protein can then be bound using a resin with glutathione. In addition to His-tag, GST-tag is another widely used affinity tag for protein purification.

Antibodies are large molecules of glycosylated proteins containing disulfide bonds, and their production is thus bound to a eukaryotic expression system, which allows to perform said post-translational modifications. For this reason, production of antibodies is relatively expensive.

Antibody molecules are also quite susceptible to degradation: as proteins they must generally be stored at low temperatures, and if necessary, frozen in aliquots. Their repeated thawing often leads to loss of their ability to bind a given antigen.

Polymers prepared by homopolymerization of N-(2-hydroxypropyl)methacrylamide (HPMA) are biocompatible, nonimmunogenic and water-soluble. Thanks to these features, HPMA copolymers are used as carriers for drugs and imaging compounds, used particularly as anticancer drugs [1-2]. HPMA copolymers are multivalent macromolecules that can be linked with various low molecular compounds, e.g. fluorescent probes, radionuclides or drugs. Besides these low-molecular substances, HPMA copolymers can be modified with (glyco)proteins, oligonucleotides and polynucleotides. Multivalence of HPMA copolymers allows to connect both just one type of molecules, and combinations of various types with different functions [3-5].

The invention describes macromolecular conjugates of polymers capable of visualization, immobilization and separation of proteins labeled with purification tags.

DISCLOSURE OF THE INVENTION

The present invention describes a macromolecular conjugate of synthetic copolymer with low molecular weight functional compounds (hereinafter also referred to as "functional groups", i.e., "binding group", "imaging probe" and "affinity tag"; this designation refers to their function in the resulting conjugate and has nothing to do with the so-called chemical functional groups). The backbone of the macromolecule (conjugate) is formed of a synthetic copolymer, to which molecules of functional groups are linked with a covalent bond: (a) at least one binding group allowing specific binding of the conjugate to a protein, and at least one (b) affinity tag and/or (c) imaging probe. Scheme of the described conjugate is shown in FIG. 1.

Water-soluble synthetic copolymers are preferred.

Preparation of the synthetic copolymer has been described previously [5-6]; polymeric conjugates are prepared from polymer precursors which contain monomers:

at least one type of monomer of Formula 1:

wherein: $R^1$ is selected from H, $CH_3$; and $R^2$ is selected from $NH_2$, $NH-CH_2-CH(OH)-CH_3$, $NH-CH_3$, $NH-CH_2CH_3$, $NH-CH_2CH_2-OH$, $NH-CH_2CH_2CH_2-OH$, $NHC(CH_2OH)_3$, $NH-CH_2CH_2-N^+(CH_3)_3Cl^-$, $O-CH_2CH_2-OH$, $O-(CH_2CH_2O)_2-H$, $O-(CH_2CH_2O)_3-H$, $O-CH_2CH_2-N^+(CH_3)_3Cl^-$, $NH-(CH_2)_3N^+(CH_3)_2-(CH_2)_2-COO^-$ and at least one type of monomer of Formula 2:

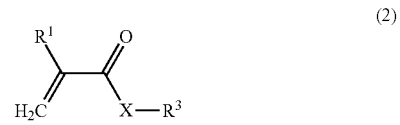

wherein: $R^1$ is selected from H, $CH_3$; and

X is selected from $NH-(CH_2)_2-CO$, $NH-(CH_2)_3-CO$, $NH-(CH_2)_4-CO$, $NH-(CH_2)_5-CO$, Gly, GlyGly, GlyPheLeuGly; and $R^3$ is selected from:

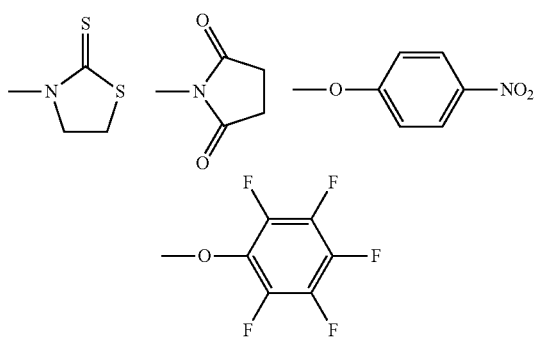

($R^3$ is a reactive group).

The content of reactive groups (i.e. content of the monomer of Formula 2) in the copolymer is preferably in the range of 0.5 to 30 mol. %, more preferably 2 to 20 mol. %.

In the polymeric conjugate, at least one $R^3$ reactive group of the copolymer is replaced by the binding group, at least one $R^3$ reactive group is replaced by the affinity tag and/or at least one $R^3$ reactive group is replaced by the imaging probe. Preferably, more than one $R^3$ reactive group is replaced by said groups. More preferably, more than 50% of the $R^3$ reactive groups are replaced, even more preferably, 100% of the $R^3$ reactive groups are replaced by said groups. Reactive groups remaining in the polymer chain after conjugation are always replaced with 1-amino-propan-2-ol group.

HPMA copolymer, i.e. poly(HPMA-co-Ma-β-Ala-TT), copolymer prepared by conventional solution radical polymerization or controlled radical copolymerization (e.g. RAFT copolymerization, reversible addition-fragmentation chain-transfer) of N-(2-hydroxypropyl)methacrylamide (HPMA) and 3-(3-methakrylamidopropanoyl)thiazolidine-2-thione (Ma-β-Ala-TT) can be preferably used as the basic copolymer. HPMA content is preferably in the range from 70 to 98 mol. %, the content of reactive thiazolidine-2-thione groups is 2 to 30 mol. %.

The functional groups are attached to the polymer chain via an amide bond, which is formed by reacting the amino group present on the molecule functional compound, i.e. precursor of the binding group, affinity tag or imaging probe and reactive group (preferably a thiazolidine-2-thione) present on the polymer chain.

The molecular weight of the conjugate is preferably in the range of 1000 to 500000 g/mol, preferably in the range from 20000 to 150000 g/mol.

The binding group is a low molecular weight substance allowing specific binding of the conjugate to a certain protein; targeting specificity of the conjugate is determined by the properties of the binding group. The binding groups were selected from compounds binding any of the commercially available protein (purification) markers (tags) such as e.g. nitrilotriacetic acid (NTA) for binding the polyhistidine tag (His-tag), or the reduced form of glutathione for binding glutathione-S-transferase (GST tag). The resulting conjugate is then applicable to any proteins that contain this marker protein.

Compounds binding His-tag are generally complexes of ions and chelating agents; the most widely used chelating agents include iminodiacetic acid (IDA), nitrilotriacetic acid (NTA) and carboxylmethylaspartate (CMA), or triNTA group which is a derivative of NTA; using multiple complexes increases the affinity of these compounds for the His-tag. The most commonly used complexes are Ni-IDA, Ni-NTA, Co-CMA. According to the properties of the studied protein, it is possible to use both native conditions and denaturing conditions for purification (e.g. in concentrated urea). After binding the protein with the conjugate containing complexes binding His-tag, it is possible to elute the protein from the resin with a solution of imidazole.

Glutathione (GSH) allows binding proteins produced in fusion with glutathione-S-transferase (GST). After binding of the fusion protein onto the conjugate with glutathione, it is possible to elute this protein from the resin with a solution of free glutathione.

The binding group may be attached to the synthetic copolymer via a flexible linker, such as a linker based on (oligo)polyethylene glycol, peptide, nucleic acid or oligosaccharide. The linker enables such binding of the binding group to the target protein, as to avoid steric hindrance of interactions between the connected ligand and other molecules. Preferably, the linker is selected from the group consisting of linkers based on polyethylene glycol, peptide, preferably a peptide having a molecular weight in the range of 100 to 5,000 g/mol, or nucleic acid, preferably a nucleic acid containing 1 to 40 nucleotides, or oligosaccharide, preferably an oligosaccharide containing 1 to 40 monosaccharides.

Affinity group may be e.g. biotin: due to the very strong interaction of biotin-avidin/streptavidin/neutravidin, the conjugate is easily immobilizable on a resin based on Streptavidin Sepharose. Thanks to the very strong biotin-avidin/streptavidin/neutravidin bond ($K_D$~$10^{-15}$), dissociation of the conjugate from the resin is virtually impossible. Other proteins conjugated with streptavidin (chemically or by genetic fusion) can be bound to the conjugate through biotin. This can be used e.g. in ELISA (binding neutravidin conjugated to horseradish peroxidase).

Besides biotin, these are other possible affinity tags: a FLAG tag (DYKDDDDK sequence recognized by an antibody), a His-tag (polyhistidine sequence bound by chelated nickel, but not in the case of His-tag-binding conjugate), a hemagglutinin tag (HA tag, YPYDVPDYA amino acid sequence derived from hemagglutinin, a surface glycoprotein of influenza virus, recognized by an antibody), a Strep-tag (WSHPQFEK octapeptide sequence bound by modified streptavidin—Strep-Tactin), an Avi-tag (peptide sequence recognized by biotinligase; biotinylation enables subsequent isolation by streptavidin), GST (glutathione-S-transferase, a glutathione-binding enzyme), a c-myc-tag (EQKLISEEDL peptide sequence recognized by an antibody), a V5-tag (GKPIPNPLLGLDST peptide sequence recognized by an antibody), an E-tag (GAPVPYPDPLEPR peptide sequence recognized by an antibody), an S-tag (KETAAAKFERQH-MDS peptide sequence recognized by an antibody), an SBP-tag (longer peptide sequence bound by streptavidin), poly(Glu)-tag (polyglutamate sequence, e.g. hexaglutamate that binds to anion exchangers), a calmodulin tag (a longer peptide sequence bound by calmodulin) or other compound capable of immobilization to a solid phase.

The imaging probe may be a fluorophore, preferably with an excitation maximum in the range of 350 to 850 nm, e.g. ATTO488 or DY676 fluorophore, enabling visualization of the polymer and the proteins or cells to which the conjugate is bound. This allows to use the conjugate in methods such as e.g. flow cytometry (and a derived technique called FACS, fluorescence-activated cell sorting, separating cells based on their fluorescence at a given wavelength), or immunocytochemistry and immunohistochemistry. For the detection of proteins by Western blotting (using systems capturing fluorescence, e.g. Odyssey CLx System) a fluorophore can be advantageously used with emission of radiation in the fer-red or near-infrared region of the spectrum ("far-red" fluorescence or "near-infrared" fluorescence) as the use of radiation with a longer wavelength significantly reduces light scattering and autofluorescence.

In another embodiment, the imaging probe may be a metal complex, e.g. lanthanide (particularly Gd, Mn or Dy, Eu). In another embodiment, the imaging probe may be a complex of a radionuclide, e.g. selected from the group consisting of $^{64}Cu$, $^{68}Ga$, $^{18}F$. In another embodiment, the imaging probe can be also a complex of a radionuclide selected from the group $^{99m}Tc$, $^{123}I$, $^{125}I$ $^{131}I$, $^{57}Co$, $^{51}Cr$, $^{67}Ga$, $^{64}Cu$, $^{111}In$, $^{90}Y$. Ligands suitable for complexation of these metals are well known in the field, such as macrocyclic ligands, derivatives of cyclopentadienyl, phosphine and azine ligands.

The present invention has several advantages over the currently used antibodies. Preparation of polymeric conjugates is relatively easy and inexpensive. The polymeric backbone, thanks to a non-protein nature of the molecules, provides enhanced chemical stability, which allows not only the use in non-physiological conditions, but also much reduced requirements for storage and handling.

Presence of multiple NTA groups on the triNTA conjugate leads to an increase in affinity and stronger binding of the conjugate to a His-tag.

Functionality of the prepared conjugates was tested in the examples of this patent, using several conventional biochemical and molecular-biological methods:

Western blotting is an immunological method enabling selective detection of proteins on the membrane after transfer from the gel after SDS-PAGE electrophoresis separating proteins according to their size. In a particular embodiment of the invention, a conjugate containing a derivative of an nitrilotriacetic acid (triNTA) is used, which (after binding nickel cations) binds to a polyhistidine sequence (His-tag). After transferring the proteins to the membrane (wet blot: 100 V/1 hour), the unoccupied sites on the membrane are blocked with 1% casein solution in PBS, and then the membrane is incubated for 1 hour at room temperature with a solution of the polymeric conjugate with triNTA recognizing the studied protein with a His-tag (concentration of the conjugate is in the range of 100 nM-100 pM). After incubation and subsequent washing, the membrane is incubated in a solution of Neutravidin conjugated to horseradish peroxidase (dilution 1:2500), binding to the biotin present on the polymeric conjugate. The amount of protein is then determined by chemiluminescence, or by fluorescence (using fluorophore present on the conjugate, then it is not necessary to add Neutravidin).

Immunoprecipitation (or "pulldown", i.e. a method analogous to the immunoprecipitation using substances other than antibodies) involves immobilizing the polymer conjugate to a solid phase, e.g. streptavidin Sepharose. Then, the resin is incubated with a sample containing the protein recognized by the conjugate. After washing the resin, the protein is released from the resin, e.g. by a change in pH, change in ionic strength, heating in the presence of SDS and so on. Another possibility is to first incubate the sample with the conjugate, and then separate the resulting complex conjugate-protein from the sample using streptavidin sepharose.

Measurement of surface plasmon resonance (SPR) is a biophysical technique to analyze the course of binding (and consequently the strength of this bond) of two interacting substances. In the first embodiment, when the protein is immobilized on a gold biosensor chip and binding of the conjugate to the protein is analyzed, it is possible to determine the dissociation constant for the protein-conjugate binding. In a second embodiment, when the polymer conjugate is used to immobilize the protein on the surface of the biosensor, it is possible to analyze binding between the given protein and another substance.

ELISA (Enzyme-Linked Immunosorbent Assay) is an immunoassay method, which in its sandwich configuration with two different substances, allows quantitation of the protein. First, the surface of the plate is coated with primary antibody against the protein and the unoccupied surface of the plate is blocked with casein solution. Then the sample is added with the protein to be determined, and after its binding to the antibody, the polymer conjugate binding this protein is added. Bound conjugate is determined using Neutravidin (conjugated with horseradish peroxidase) binding biotin present on the conjugate. Besides this method of (chemiluminescent) determination, the conjugate may also be determined by fluorescence of the fluorophore present on the conjugate. Alternatively to the above ELISA procedure, also the polymeric conjugate can be immobilized by binding to neutravidin/streptavidin adsorbed on the surface of the plate (through biotin-streptavidin bond). After binding of the protein to be determined, biotinylated primary antibody against the protein is added, which is then determined using Neutravidin again (conjugated with horseradish peroxidase) binding biotin present on the antibody. Biotin present on the conjugate can thus be used both for immobilization and for detection, while a fluorophore just for detection.

The conjugates are designed for isolation, visualization, and immobilization of recombinant proteins in biochemical and molecular-biological methods, such as e.g., ELISA, immunoprecipitation (or "pull-down" when a substance other than antibody is used), Western blotting, surface plasmon resonance, and others. It is also possible to use the immobilization of proteins for screening compounds binding to these proteins.

The invention was developed under the project "Management of the structure and function of biomolecules at the molecular level: the interplay between theory and experiment," Center of Excellence GACR, P208/12/016.

11: Elution: Conjugate 4; 12: Elution: control without polymer. All lanes of each fraction were loaded with 5 μl sample.

Figure 9:
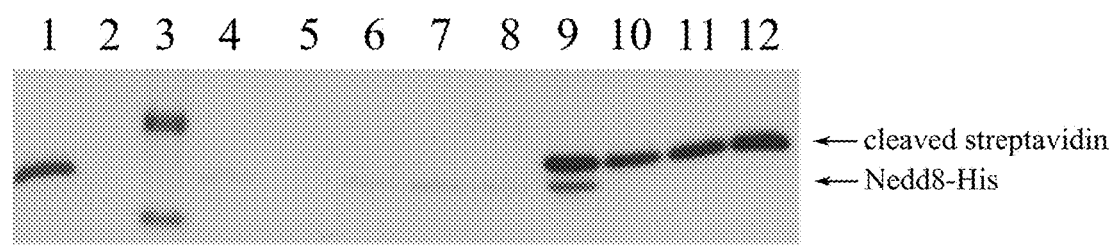
FIG. 9A shows affinity isolation ("pull-down") of a protein containing His-tag (NEDD8-HisTag) using Conjugate 1 under native conditions. Proteins were separated by SDS-PAGE electrophoresis and the gel was stained with silver. Lane 1: NEDD8-His Tag (500 ng); 2: Conjugate 1 (25 µg); 3: All Blue Marker (2 µl); 4: Load; 5: FT: Conjugate 1; 6: FT: Conjugate 3; 7: FT: Conjugate 4; 8: FT: control without polymer; 9: Elution: Conjugate 1; 10: Elution: Conjugate 3.
Figure 9:
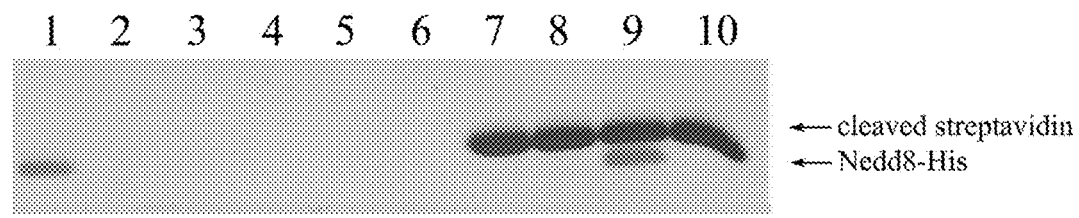

FIG. 9B shows affinity isolation ("pull-down") of a protein containing His-tag (NEDD8-HisTag) using Conjugate 1 under denaturing conditions. Proteins were separated by SDS-PAGE electrophoresis and the gel was stained with silver. Lane 1: NEDD8-His Tag (500 ng); 2: Load; 3: FT: Conjugate 3; 4: FT: Conjugate 4; 5: FT: Conjugate 1; 6: FT: control without polymer; 7: Elution: Conjugate 3; 8: Elution: Conjugate 4; 9: Elution: Conjugate 1; 10: Elution: control without polymer. All lanes of each fraction were loaded with 5 μl sample.

Figure 10:
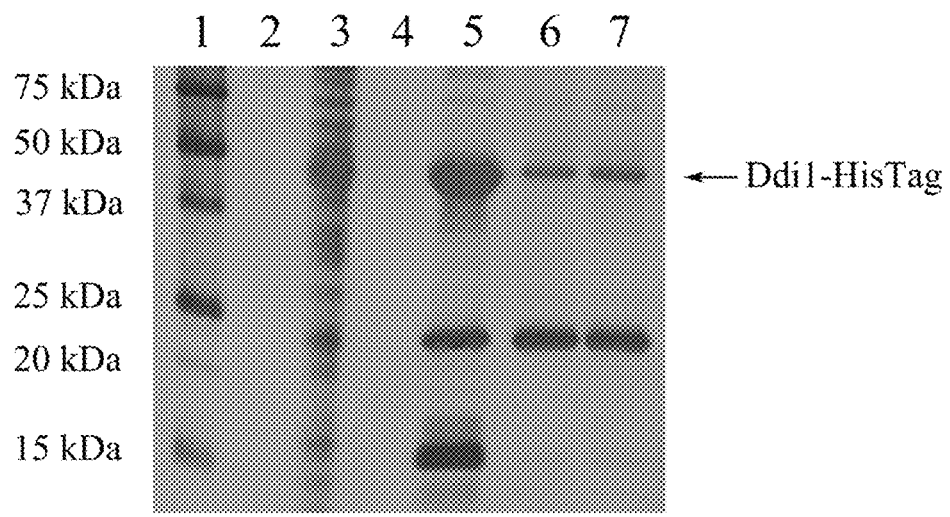

FIG. 10 shows affinity isolation ("pull-down") of a protein containing His-tagg (Ddi1-HisTag) from bacterial lysate using Conjugate 1. Proteins were separated by SDS-PAGE electrophoresis and the gel was stained with silver. Track 1: All blue marker (2 μl); 2: free lane; 3: Load; 4: free lane; 5: The elution: Conjugate 1; 6: Elution: Conjugate 3; 7: Elution: control without polymer. All lanes of each fraction were loaded with 5 μl sample.

Figure 11:
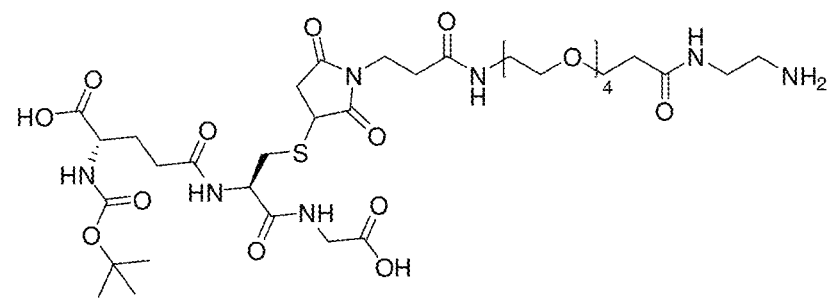

FIG. 11 shows the structure of Compound B designed for the targeting of protein GST-tag.

Figure 12:
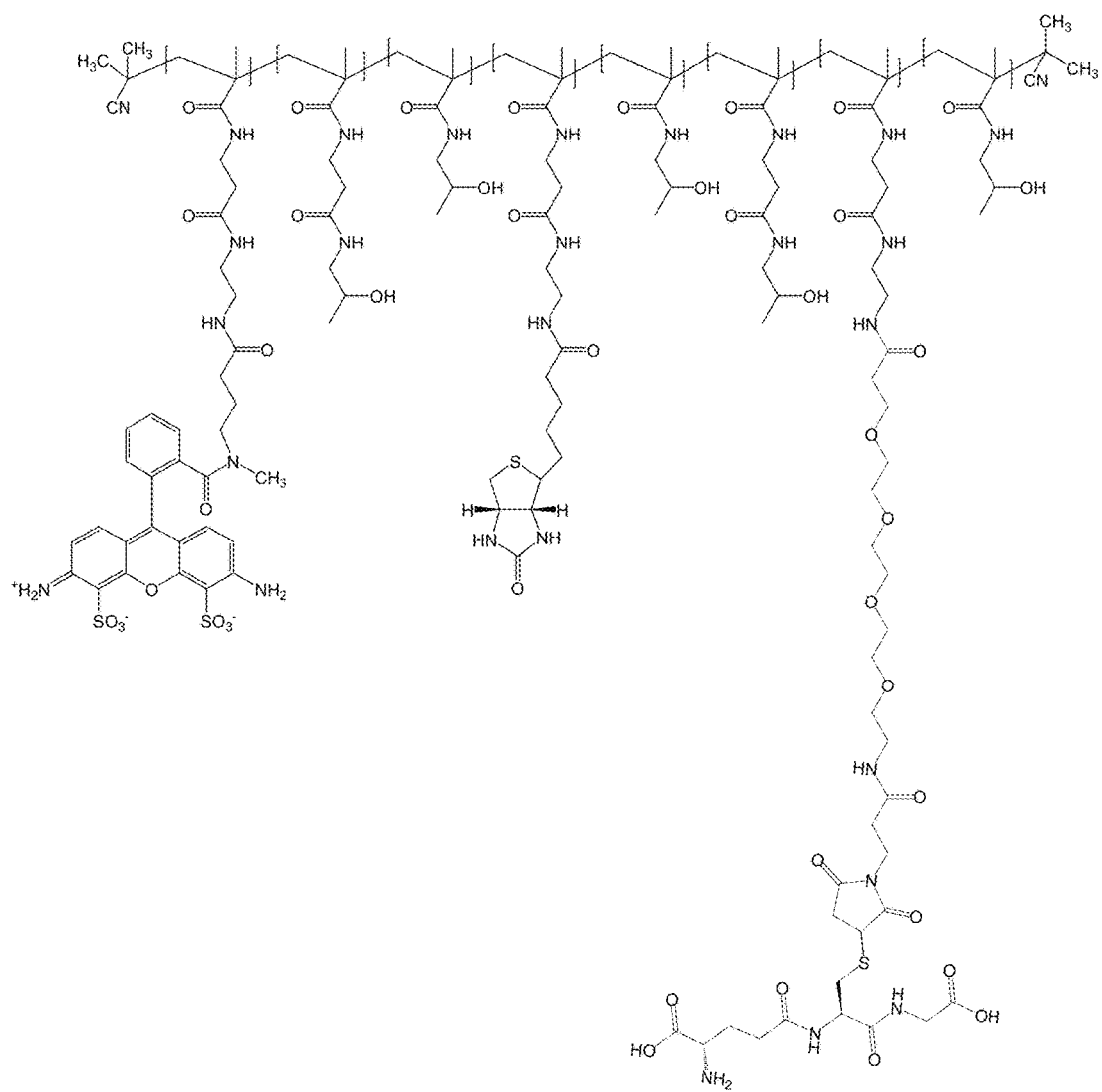

FIG. 12 shows the structure of Conjugate 5 designed for the targeting of proteins with GST-tag.

Figure 13:
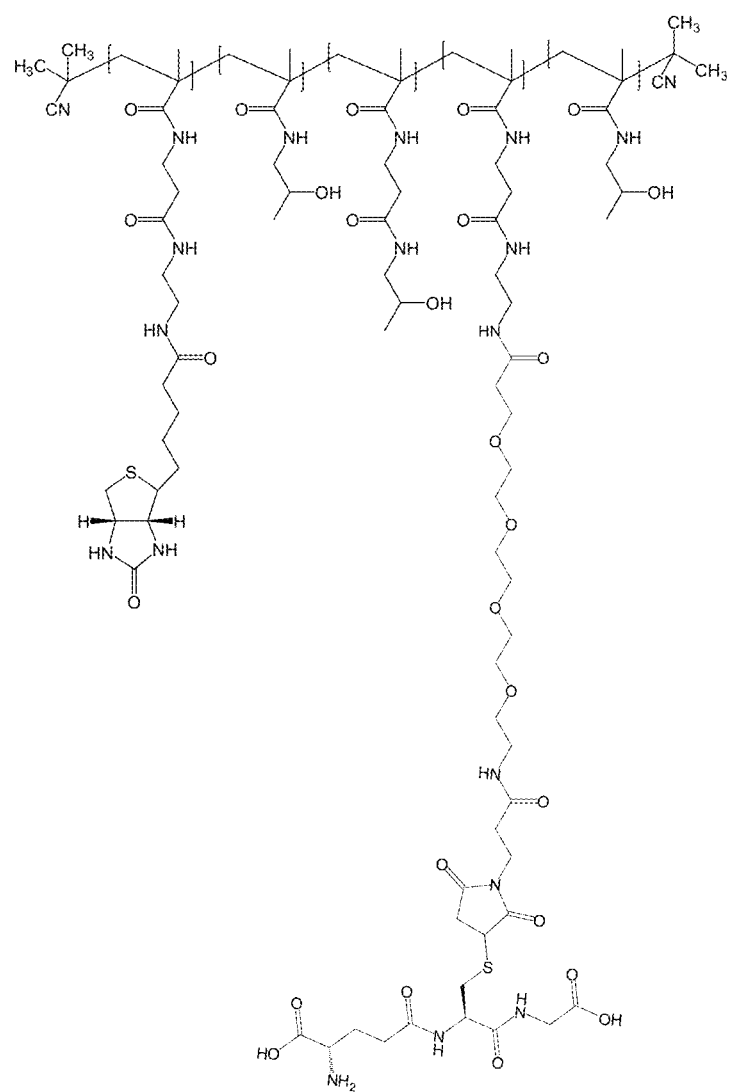

FIG. 13 shows the structure of Conjugate 6 designed for the targeting of proteins with GST-tag.

EXAMPLES OF CARRYING OUT THE INVENTION

All chemicals used were from Sigma-Aldrich unless stated otherwise. All compounds tested in biological assays were purified using Waters Delta 600 preparative HPLC system (flow rate 7 ml/min; gradient shown for each compound, including retention times), with Waters SunFire C18 OBD Prep Column, 5 μm, 19×150 mm. Purity of compounds was checked on an analytical Jasco PU-1580 HPLC system (flow rate 1 ml/min with a constant gradient of 2-100% acetonitrile in 30 minutes; retention time is shown for each compound) with Watrex C18 Analytical Column, 5 μm, 250×5 mm. Final compounds were at least of 99% purity and their structure was further confirmed using HR-MS on LTQ Orbitrap XL (Thermo Fisher Scientific) and NMR (Bruker Avance I™ 500 MHz equipped with a cryo-probe). All interaction constants are given in Hz.

Example 1: Preparation of Compound A

Compound A was prepared according to the following scheme:

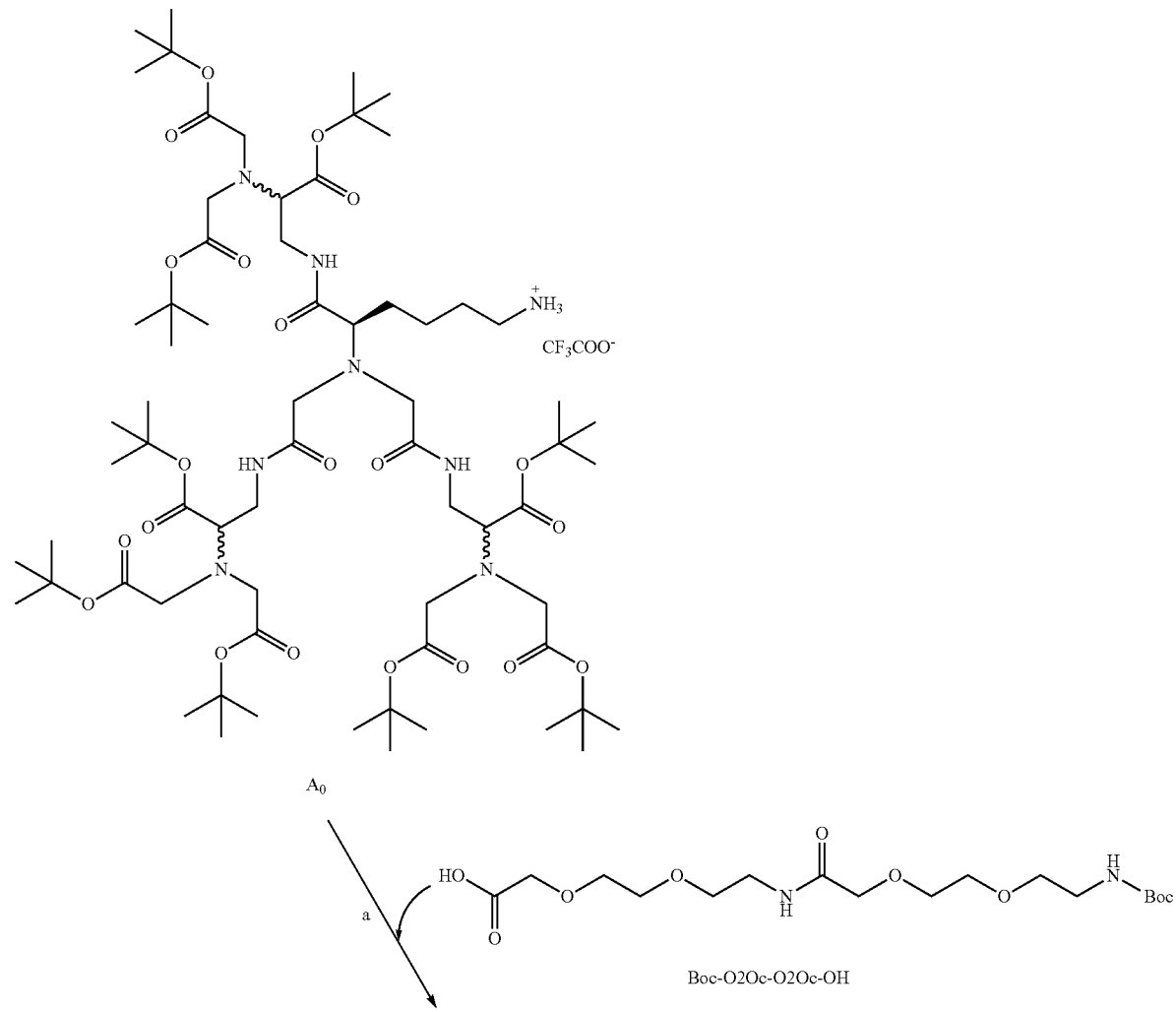

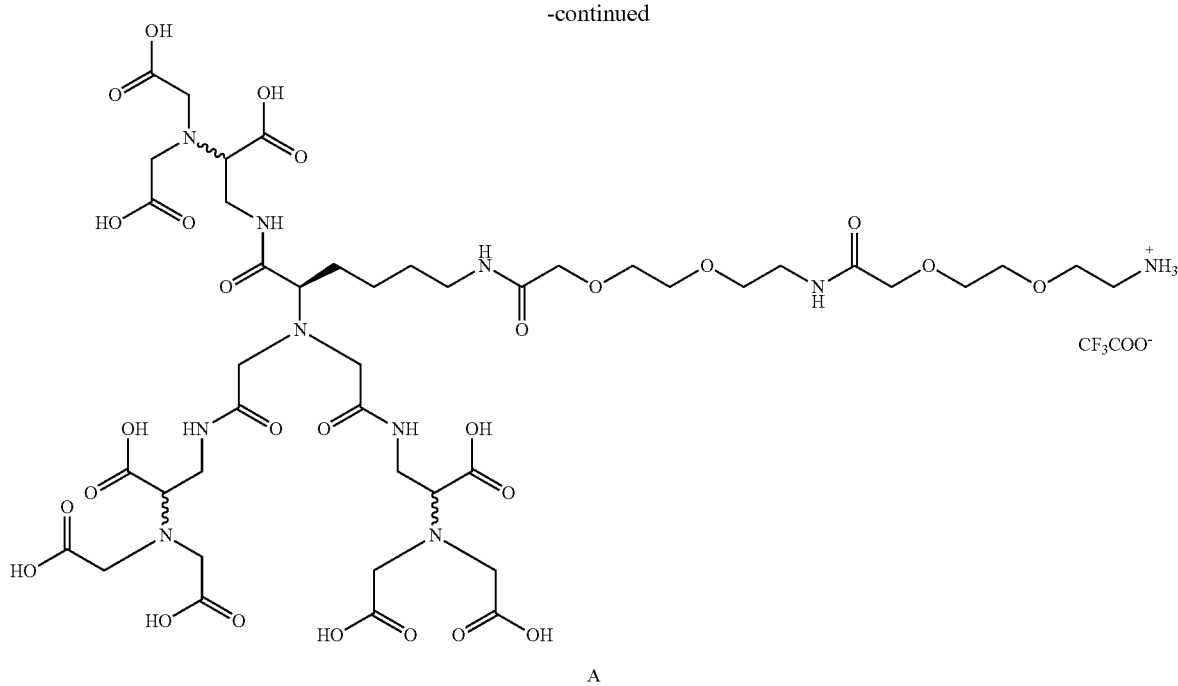

A a 1) DCC, DMF;
2) TFA (1) Compound $A_0$

Compound $A_0$, $NH_2$-triNTA(o-tBu)$_9$: Synthesis of Compound $A_0$ was performed according to published procedure [7], with a small deviation in one step: in a reaction between a derivative of a tricarboxylic acid (derived from lysine), and three monomers of nitrilotriacetic acid, N,N,N',N'-tetramethyl-O—(N-succinimidyl)uronium tetrafluoroborate (TSTU) was used as the activating agent instead of NHS/EDC, as TSTU provided significantly higher yields.

(2) Compound A

Compound A, $NH_2$—$PEG_5$-triNTA: Compound $A_0$ (52 mg, 38 μmol, 1.0 eq, purified using HPLC prior to this step) was dissolved in 1 ml of DMF to which 15 mg (38 μmol, 1.0 eq) of Boc-O2Oc-O2Oc-OH linker (Iris Biotech, #BAA1485) was subsequently added in one step. 16 mg (76 μmol, 2.0 eq) of DCC was further added to the reaction mixture and the reaction was left to react for 24 hours at room temperature. The solvent was evaporated and the raw mixture was mixed with 1 ml of pure TFA; the reaction mixture was alternately stirred and sonicated in a water bath for 3 hours. The TFA was removed with nitrogen gas and the final product was purified by preparative HPLC (gradient 2-30% ACN in 50 min, $R_T$=35 min). The weight of the obtained pure product was 4 mg (yield=32%).

Analytical HPLC (gradient 2-100%, 30 min) RT=12.0 min. HR-MS (ESI+): counted for $C_{43}H_{71}O_{27}N_{10}$ [M]$^+$ 1159.44846. Found 1159.44849.

Example 2: Preparation of Conjugate 1

(1) Preparation of the Polymeric Precursor Poly(HPMA-Co-Ma-β-Ala-TT)

Monomeric compounds N-(2-hydroxypropyl) methacrylamide (HPMA) and 3-(3-methacrylamido propanoyl) thiazolidine-2-thione (Ma-β-Ala-TT) were prepared according to a published procedure [1, 5]. The polymeric precursor poly(HPMA-co-Ma-β-Ala-TT) was prepared using RAFT-copolymerization (reversible addition-fragmentation chain-transfer). 1.0 g of HPMA (85% mol) was dissolved in 7.3 ml of tert-butanol; 318 mg of Ma-β-Ala-TT (15% mol) dissolved in 1.9 ml of DMSO, 2.42 mg of 2-cyano-2-propyl-benzodithioate and 0.90 mg of 2,2'-azobis (2-methylpropionitrile) was added to the solution and the solution was transferred into a polymerization vial. The mixture was purged with argon for 10 min and then the vial was sealed. The polymerization reaction was performed at 70° C. (16 h). The polymeric precursor was isolated by precipitation into acetone:diethyl ether mixture (3:1), filtered, washed with acetone and diethyl ether and dried in vacuum. Dithiobenzoate end groups were removed according to a previously published procedure [8].

This procedure resulted in the polymeric precursor poly (HPMA-co-Ma-β-Ala-TT) with molecular weight of $M_w$=81600 g/mol, polydispersity Đ=1.18 and containing 14.6 mol % of reactive thiazolidin-2-thione (TT) groups.

(2) Preparation of Conjugate 1

The polymeric precursor poly(HPMA-co-Ma-β-Ala-TT) (0.040 g, $M_w$=81600 g/mol, 14.6 mol % TT), Compound A (6.0 mg) and N-(2-aminoethyl) biotinamido hydrobromide (biotin-$NH_2$) (5 mg) was dissolved in 0.2 ml of DMSO. ATTO488-$NH_2$ (2.5 mg) was dissolved in 0.1 ml of DMSO and added to a solution of the polymeric precursor. N,N-diisopropylethylamine (DIPEA) (8.0 μl) was added and the reaction mixture was stirred for 4 hours at room temperature. Subsequently, 1-amino-propan-2-ol (5 μl) was added to the solution and the reaction mixture was stirred for 10 min. Then, the polymeric conjugate 1 poly(HPMA-co-Ma-β-Ala-CompoundA-co-Ma-β-Ala-ATTO488-co-Ma-β-Ala-NH-biotin) was isolated by precipitation in acetone:diethyl ether (3:1), filtered, washed with acetone and diethyl ether and dried in vacuum. Polymeric conjugate was purified from low-molecular impurities by column chromatography on Sephadex LH-20 in methanol, precipitated in diethyl ether, filtered and dried in vacuum. The yield of Conjugate 1 was 22 mg. Content of ATTO488 4.17% was determined spectrophotometrically ($\varepsilon_{502nm}$=90000 l·mol$^{-1}$·cm$^{-1}$, distilled water) and the inhibitor content 11.28% was determined in the sample hydrolysate (6N—HCl, 115° C., 16 hr) by HPLC with fluorescence detector (Ex. 229 nm, Em. 450 nm), column: Chromolith C18, precolumn derivatisation method with o-phthaldialdehyde.

(3) Preparation of Conjugate 3 (Comparative Conjugate Serving as a Negative Control)

The polymeric precursor poly(HPMA-co-Ma-ß-Ala-TT) for the preparation of Conjugate 3 was prepared by RAFT-copolymerization as described in Example 2 (see above), using the following composition of the polymerization mixture: 500 mg of HPMA (85 mol %), 159 mg of Ma-ß-Ala-TT (15 mol %) dissolved in 0.8 ml of DMSO, 1.21 mg of 2-cyano-2-propylbenzodithioate and 0.45 mg 2,2'-azobis(2-methylpropionitrile) were dissolved in 3.8 ml of tert-butanol. This procedure resulted in the polymeric precursor poly(HPMA-co-Ma-β-Ala-TT) with a molecular weight $M_w$=85900 g/mol and a polydispersity of Đ=1.22 and containing 13.4 mol % of the reactive thiazolidine-2-thione groups.

The polymeric precursor poly(HPMA-co-Ma-β-Ala-TT) (0.045 g, $M_w$=85900 g/mol, 13.4 mol % TT) and 5 mg of biotin-NH$_2$ was dissolved in 0.2 ml of DMSO. ATTO488-NH$_2$ (2.5 mg) was dissolved in 0.1 ml of DMSO and added to the solution of polymeric precursor. N,N-diisopropylethylamine (DIPEA) (2.5 µl) was added and the reaction mixture was stirred for 4 hours at room temperature, then 1-amino-propan-2-ol (5 µl) was added to the solution and the reaction mixture was stirred for 10 min. Then, the polymeric conjugate 3 poly(HPMA-co-Ma-β-Ala-ATTO488-co-Ma-β-Ala-NH-biotin) was isolated by precipitation into acetone:diethyl ether (3:1), filtered, washed with acetone and diethyl ether and dried in vacuum. Polymeric conjugate was purified by column chromatography on Sephadex LH-20 in methanol, precipitated in diethyl ether, filtered and dried in vacuum. The yield of Conjugate was 3 was 32 mg, content of ATTO488 was 5.1%, and the content of biotin 10.8%.

Example 3: Preparation of Conjugate 2

(1) Preparation of Conjugate 2

The polymeric precursor poly(HPMA-co-Ma-β-Ala-TT) (0.030 mg, $M_w$=81600 g/mol, 14.6 mol % TT; see Preparation of Conjugate 1), Compound A (3.5 mg) and N-(2-aminoethyl)biotinamido hydrobromide (biotin-NH$_2$) (4 mg) were dissolved in 0.3 ml of DMSO. N,N-diisopropylethylamine (DIPEA) (4.0 µl) was added and the reaction mixture was stirred for 4 hours at room temperature; then, 1-amino-propan-2-ol (2 µl) was added to the solution and the reaction mixture was stirred for 10 min. Then, the polymeric conjugate 2 poly(HPMA-co-Ma-β-Ala-CompoundA-co-Ma-β-Ala-NH-biotin) was isolated by precipitation into acetone:diethyl ether (3:1), filtered, washed with acetone and diethyl ether and dried in vacuum. Polymeric conjugate was purified from low-molecular impurities by column chromatography on Sephadex LH-20 in methanol, precipitated in diethyl ether, filtered and dried in vacuum. The yield of Conjugate 2 was 21 mg. Biotin content 5.53% was determined using the HABA/Avidin kit (Sigma) and the inhibitor content of 10.43% was determined in the sample hydrolysate (6N—HCl, 115° C., 16 hours) by HPLC with fluorescence detector (Ex. 229 nm, Em. 450 nm), column: Chromolith C18, precolumn derivatisation method with o-phthaldialdehyde.

(2) Preparation of Conjugate 4 (Comparative Conjugate Serving as a Negative Control)

The polymeric precursor poly(HPMA-co-Ma-ß-Ala-TT) for the preparation of Conjugate 4 was prepared by RAFT-copolymerization as described in Example 2 (see above), using the following composition of the polymerization mixture: 500 mg of HPMA (90% mol), 100 mg of Ma-ß-Ala-TT (10% mol), 4.29 mg of 2-cyano-2-propylbenzodithioate, 1.59 mg of 2,2'-azobis(2-methylpropionitrile) and 4.5 ml of tert-butanol. This procedure resulted in polymeric precursor poly(HPMA-co-Ma-ß-Ala-TT) with a molecular weight of $M_w$=26600 g/mol and a polydispersity of Đ=1.07 and containing 10.4 mol % of the reactive thiazolidine-2-thione groups.

The polymeric precursor poly(HPMA-co-Ma-β-Ala-TT) (0.04 g, $M_w$=26600 g/mol, 10.4 mol % TT) was dissolved in 0.25 ml of DMSO, 5 mg of biotin-NH$_2$ was added to the solution. N,N-diisopropylethylamine (DIPEA) (3.0 µl) was then added. The compounds reacted together for 4 hours at room temperature and then 1-amino-propan-2-ol (5 µl) was added to the solution. Polymeric conjugate 4 poly(HPMA-co-Ma-β-Ala-NH-biotin) was isolated by precipitation into acetone:diethyl ether (3:1), filtered, washed with acetone and diethyl ether and dried in vacuum. Polymeric conjugate was purified by column chromatography on Sephadex LH-20 in methanol, precipitated in diethyl ether, filtered and dried in vacuum. The yield of Conjugate 4 was 28 mg and biotin content was 6.4%.

Example 4: Visualization of Proteins with His-Tag by Western Blot Using Conjugates 1 and 2

Before use, Conjugate 1 and Conjugate 2 (30 µM, 100 µl) were first incubated for 1 hour at room temperature in the presence of 94 mM nickel chloride (i.e. in a 100 fold molar excess of nickel cations to NTA groups) for filling the binding groups with nickel cations. The unbound cations were then removed by dialysis using Slide-A-Lyzer Mini Dialysis Devices (10 kDa MWCO). Dialysis was carried out at room temperature first for 3 hours, against 5 l of distilled water and then for 12 hours against 3 l of TBS.

Various amounts (0.1-10 ng) of purified recombinant M1 protein from influenza virus labeled with His-tag (M1-HisTag) was applied on SDS-PAGE electrophoresis; after electrophoresis, the gel was blotted on a membrane (wet blot: 100 V/60 min). The surface of the membrane was then blocked using 1.1% (w/v) solution of casein in PBS (Casein Buffer 20×-4× Concentrate, SDT) at room temperature for 1 hour. To visualize the M1-HisTag protein, membrane was incubated with 5 nM Conjugate 1 in PBS containing 0.05% Tween 20 (PBST), or with antibody against His-tag conjugated with horseradish peroxidase (Sigma, #A7058-1VL; 1:2000 in PBST) at room temperature for 1 hour. The blots (incubated in a solution of a Conjugate 1) were then washed three times with PBST and incubated for 1 h with NeutrAvidin conjugated to horseradish peroxidase (Thermo Scientific, #31001, 1:2500 in PBST). Finally, the blots were washed three times with PBST, and SuperSignal West Classic/Dura/Femto Chemiluminescent Substrate (Thermo Scientific) was applied to the membrane. Chemiluminescence was recorded using ChemiDoc It™-600 Imaging System (UVP).

Figure 1:
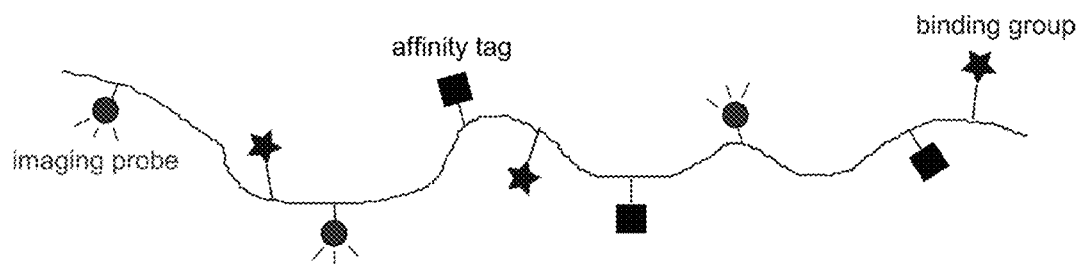
FIG. 1 shows a schematic structure of the polymeric conjugates.
Figure 2:
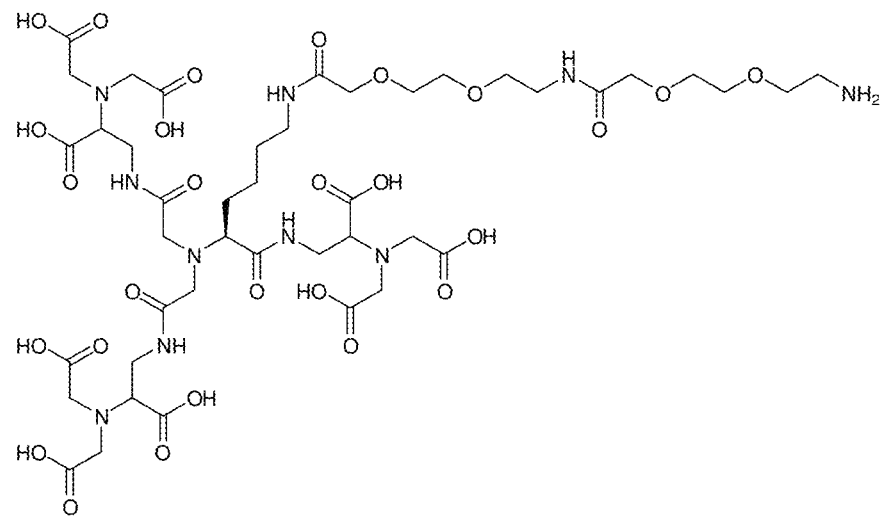
FIG. 2 shows the structure of Compound A intended for targeting of the protein His-tag.
Figure 3:
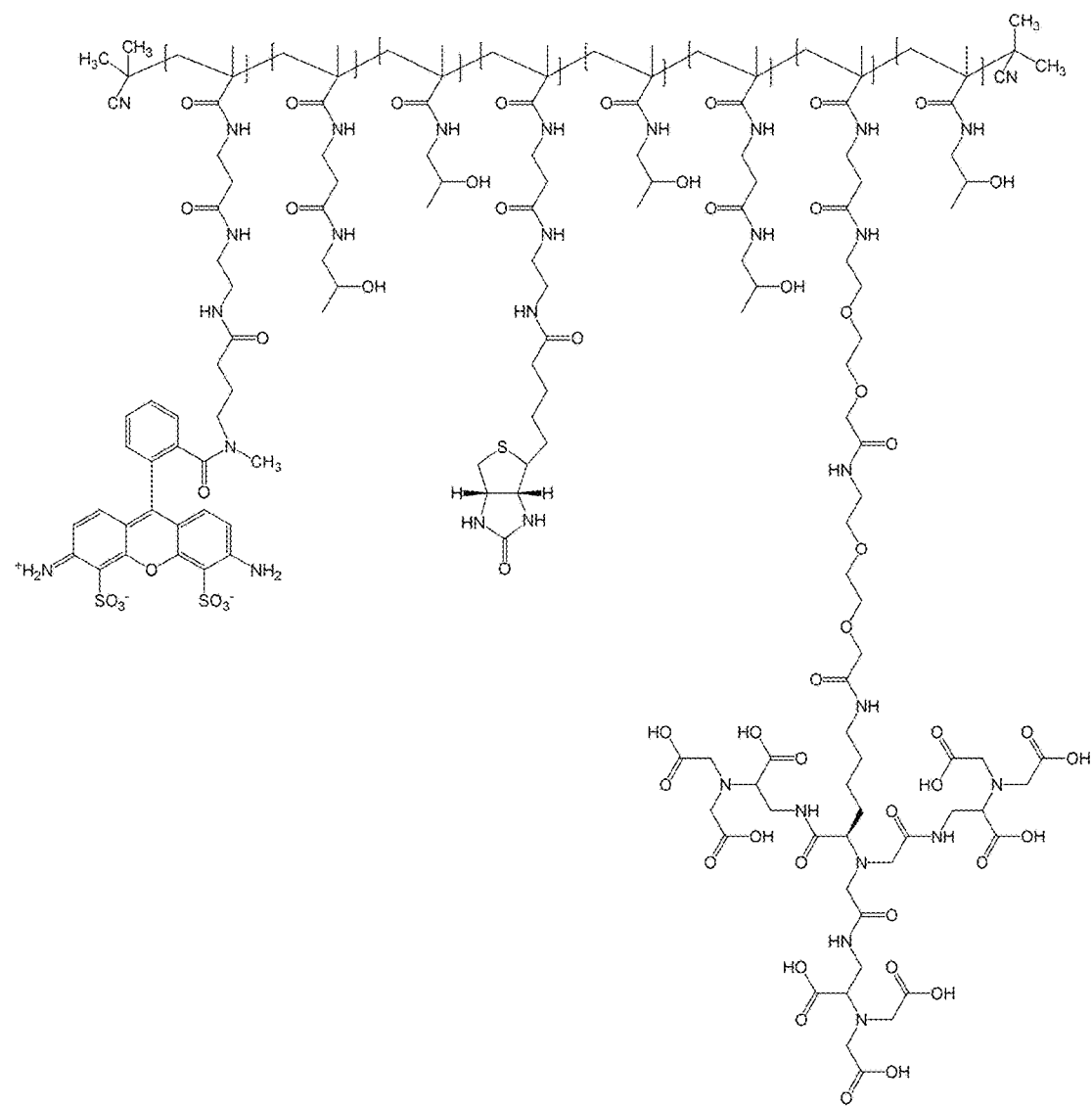
FIG. 3 shows the structure of Conjugate 1 intended for targeting of proteins with a His-tag.
Figure 4:
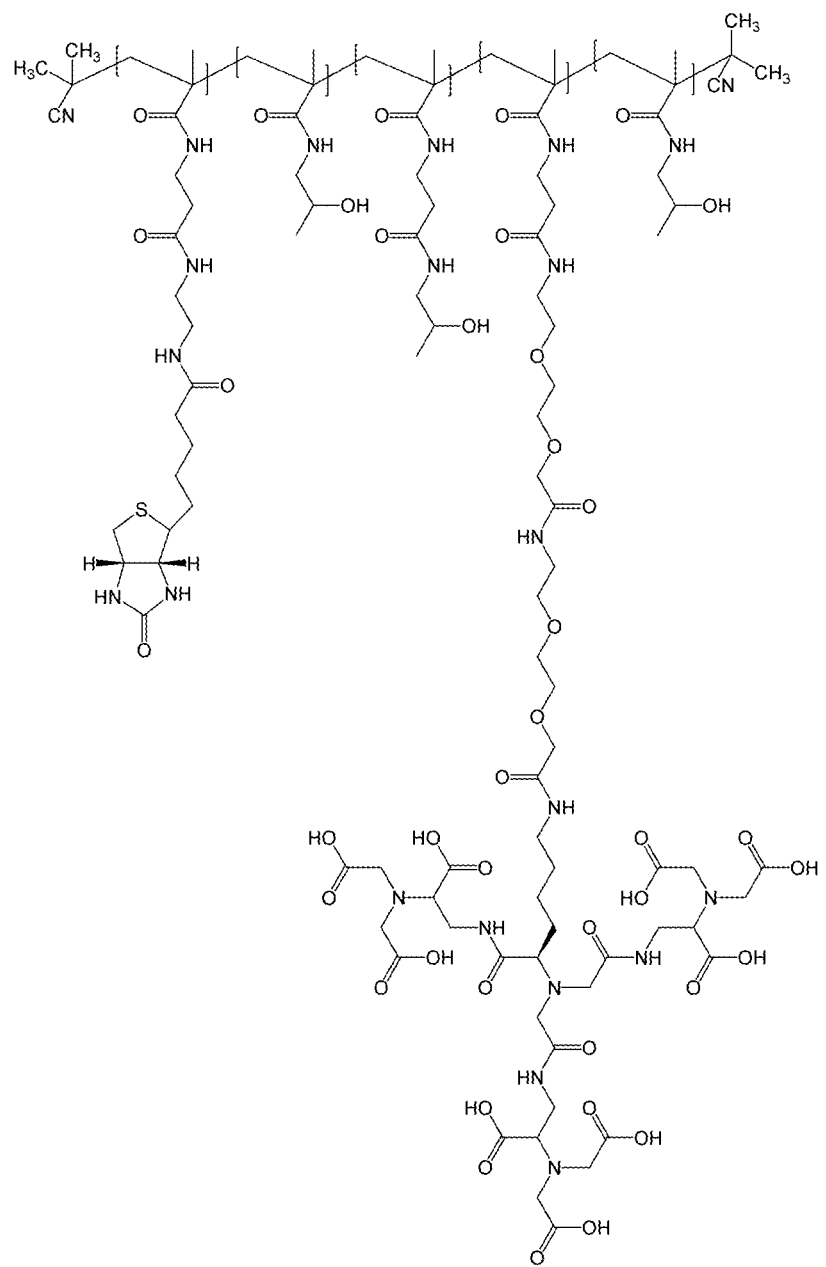
FIG. 4 shows the structure of Conjugate 2 intended for targeting proteins with a His-tag.
Figure 5:
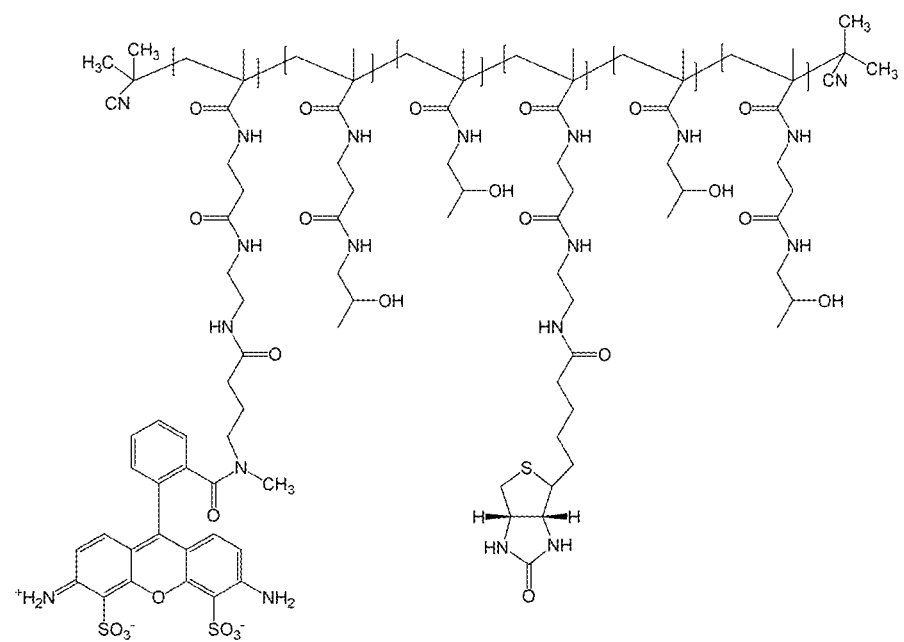
FIG. 5 shows the structure of Conjugate 3 without a binding group (negative control).
Figure 6:
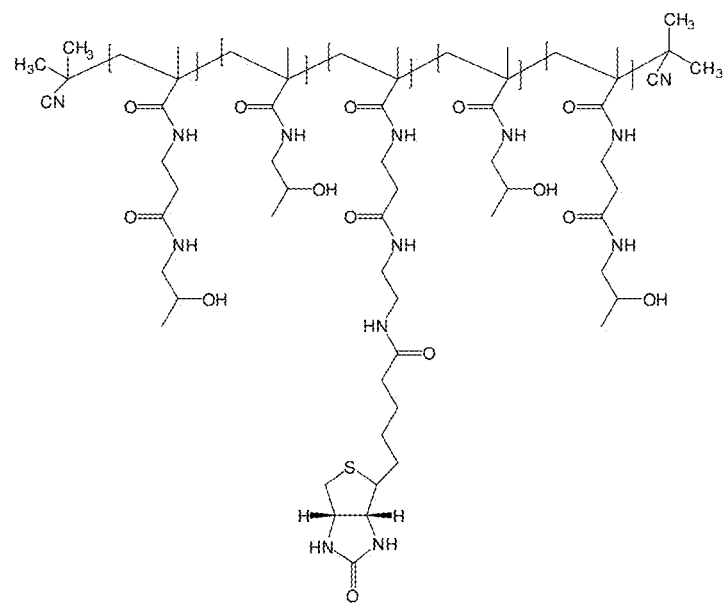
FIG. 6 shows the structure of Conjugate 4 without a binding group (negative control).
Figure 7:
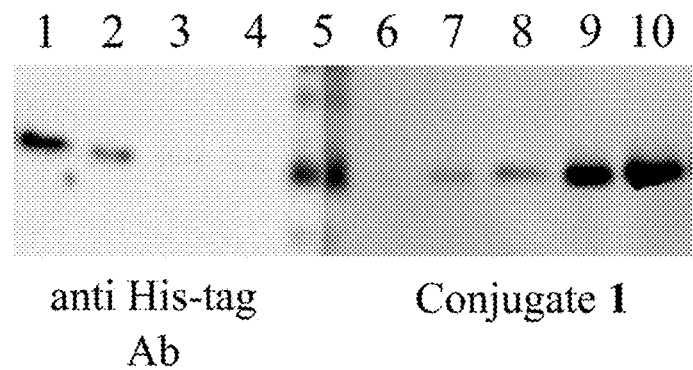
FIG. 7 shows a Western blot with recombinant purified M1 protein from influenza virus labeled with His-tag (M1-HisTag), which was visualized using a commercial antibody against His-tag and Conjugate 1. Lane 1: M1-HisTag (10 ng); 2: M1-HisTag (5 ng); 3: M1-HisTag (1 ng); 4: M1-HisTag (0.5 ng); 5: All blue marker (2 µl); 6: M1-HisTag (0.1 ng); 7: M1-HisTag (0.5 ng); 8: M1-HisTag (1 ng); 9: M1-HisTag (5 ng); 10: M1-HisTag (10 ng).

When comparing the detection sensitivity of the recombinant purified M1-HisTag protein using 5 nM Conjugate 1 and a commercial antibody (FIG. 7), it is clear that the detection method using Conjugate 1 is more sensitive than with the antibody (approximately 5 times) and thus has a lower limit of detection (100 pg vs. 500 pg).

Figure 8:
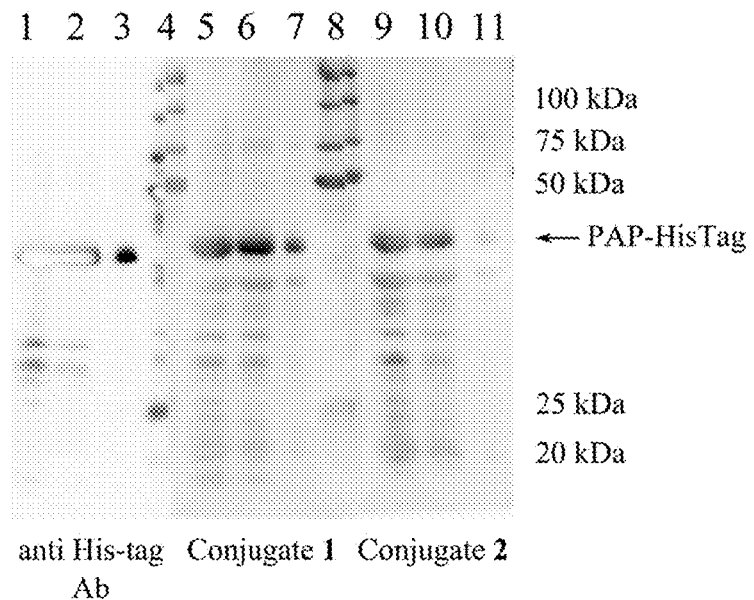
FIG. 8 shows a Western blot with bacterial lysate containing an E. coli poly(A)-polymerase labeled with HisTag (PAP-HisTag) which was visualized both with commercial antibody against His-tag, and with Conjugate 1 and Conjugate 2. Lane 1: bacterial lysate (10 µl); 2: bacterial lysate (5 µl); 3: bacterial lysate (1 µl); 4: All blue marker (2 µl); 5: bacterial lysate (10 µl); 6: bacterial lysate (5 µl); 7: bacterial lysate (1 µl); 8: All blue marker (2 µl); 9: bacterial lysate (10 µl); 10: bacterial lysate (5 µl); 11: bacterial lysate (1 µl).

Nonspecific reactivity of Conjugate 1 and Conjugate B on the Western blot was tested using a bacterial lysate containing a poly(A)-polymerase from E. coli labeled with His-tag (PAP-HisTag) (FIG. 8).

Example 5: Affinity Isolation ("Pull-Down") of NEDD8 Protein Labeled with His Tag (NEDD8-HisTag) Using Conjugate 1

Affinity isolation of the NEDD8-HisTag protein was performed both under native conditions in 20 mM Tris-HCl, 150 mM NaCl, 0.1% Tween 20, pH 7.4 (TBST) and under denaturing conditions in 8 M urea, 20 mM Tris-HCl, 300 mM NaCl, pH 7.4.

Conjugate 1, Conjugate 3 and Conjugate 4 (i.e. negative controls showing nonspecific binding; only pure resin without any added conjugate was used as the fourth sample) were pre-bound to 20 µl of Streptavidin Sepharose (200 nM solution in 1000 µl of TBST containing 1 mM $NiCl_2$, 1 hour, 6° C.). After washing with 3×1000 µl TBST, the resin was mixed with 1000 µl of a solution of NEDD8-HisTag (5 ng/µl, either under native or denaturing conditions) and incubated at 6° C. for 3 hours. The resin was then washed with 3×1000 µl TBST and subsequently, proteins were eluted by addition of 50 µl of sample buffer for SDS-PAGE and heating to 98° C. for 10 min.

NEDD8-HisTag protein was successfully isolated using Conjugate 1 both under native conditions (FIG. 9A) and under denaturing conditions (FIG. 9B). Each of the negative controls (conjugate without inhibitor; conjugate without inhibitor and ATTO488; empty resin Streptavidin Sepharose) showed that binding NEDD8-HisTag takes place specifically via Compound A with the NTA groups.

Example 6: Affinity Isolation ("Pull-Down") of the Protein Marker Ddi1 with His-Tag (Ddi1-HisTag) from the Bacterial Lysate Using Conjugate 1

Affinity isolation of Ddi1 protein (DNA-damage inducible protein 1), labeled with His tag (Ddi1-HisTag) was performed using Conjugate 1 form bacterial lysate containing Ddi1-HisTag protein (FIG. 10).

Conjugate 1, Conjugate 3 (i.e. negative control showing nonspecific binding; only pure resin without any added conjugate was used as the third sample) were pre-bound to 30 µl of Streptavidin Agarose (200 nM solution in 1000 µl of TBST for 1 h, containing 1 mM $NiCl_2$). After washing with 3×1000 µl TBST, the resin was mixed with 1000 µl of Ddi1-HisTag solution and incubated at room temperature for 1 hour. The resin was then washed with 3×1000 µl TBST and proteins were then eluted by addition of 30 µl of 250 mM imidazole and incubating for 30 min.

Ddi1-HisTag protein was successfully isolated by Conjugate 1 from bacterial lysate (FIG. 10). Besides the Ddi1-HisTag protein, the elution fraction contained two other proteins: the presence of one (~15 kDa) was given by the non-specificity of the triNTA group, the second (~22 kDa) by binding of this protein to the Streptavidin Agarose resin.

Example 7: Immobilization of Recombinant Human GCPII Labeled with His-Tag (his-rhGCPII) and the Subsequent Testing of the Inhibitory Potency of GCPII Inhibitors 10 µl solution of streptavidin (10 µg/µl) in 100 mM borate buffer, pH 9.5, was applied to the bottom of wells in a 96 well FrameStar 480/96 plate and incubated at room temperature for 1 hour.

The contents of wells was then tapped out and wells were washed three times with 200 µl of TBS. Unoccupied surface of the wells was blocked with 0.55% (w/v) solution of casein in TBS (Casein Buffer 20×-4× Concentrate, SDT, 24 h). After further washing with 3×200 µl TBST, Conjugate 2 or 4 (100 nM in TBST containing 1 mM $NiCl_2$, 2 h) was bound to streptavidin. Unbound conjugates were washed away by washing with 3×200 µl of TBST and a solution of recombinant His-rhGCPII in TBST (10 ng/well, 1 hr, prepared according to [9]) was subsequently added to the wells. After washing with 3×200 µl of TBST, either detection probe ssPSMA alone (1 nM in TBST) binding to the active site of His-rhGCPII, or a mixture of this probe and a selected test substance in a selected concentration (typically 100 µM in TBST) were added. After incubation for 1 hr at room temperature, the wells were washed 5×200 µl of TBST and the amount of bound detection probe was then determined by qPCR. From the changes in the amount of bound probe in wells incubated with test compound compared to wells incubated with the probe alone, the fraction of active sites of the His-rhGCPII occupied by a given test substance was calculated, and consequently the inhibition constant of the substance (a detailed description of the ssPSMA detection probe and a method to calculate the inhibition constants are given in Czech patent application PV 2014-527).

With this method, it was possible to determine the inhibition constant of the tested inhibitor by measuring the sample in a single well; this method was used to measure twenty inhibitors and $K_i$ values obtained corresponded to the $K_i$ values acquired by measuring His-rhGCPII enzyme kinetics.

In this patent application, conjugates have been described containing nitrilotrisacetic acid (NTA) based compounds binding polyhistidine sequence (His-tag), which is used as a purification and visualization tag for a large part of recombinantly prepared proteins. Thanks to NTA His-tag binding is therefore possible to use these conjugates universally for all proteins carrying this affinity tag. Dissociation constant for binding of the conjugate to His-tag was determined by SPR. Further, conjugates were used for isolation and purification of proteins labeled with His-tag, both under native and denaturing conditions. When using the conjugate in the Western blot method, it was possible to detect very small quantities of proteins transferred to the membrane after SDS-PAGE electrophoresis. The detection limit on Western blot using a 5 nM solution of Conjugate 1 was about 100 pg. Conjugate was further used for immobilization of proteins with His-tag in assays derived from ELISA (sandwich arrangement), where proteins after immobilization via a His-tag were incubated in the presence of a test substance and their known ligand/inhibitor (or generally a substance binding to the protein), thereby to determine the bond strength of the tested substances with the protein and thus their inhibitory potency.

Example 8: Preparation of Compound B
Compound B was prepared according to the following scheme:
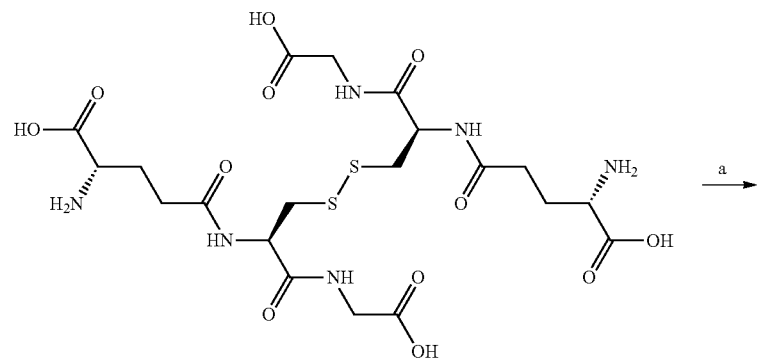
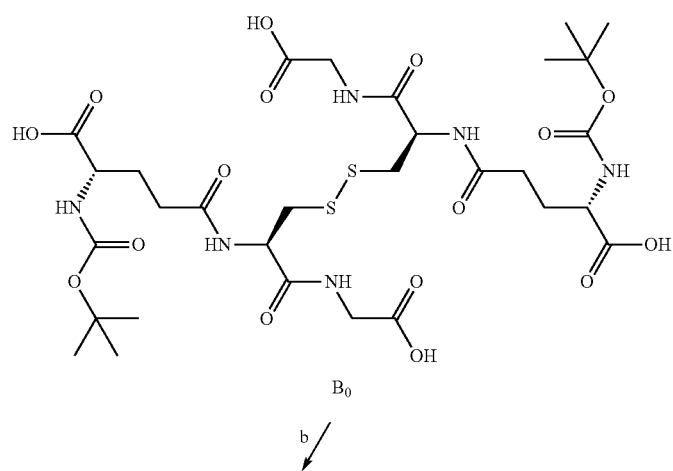
$B_0$
b ↓
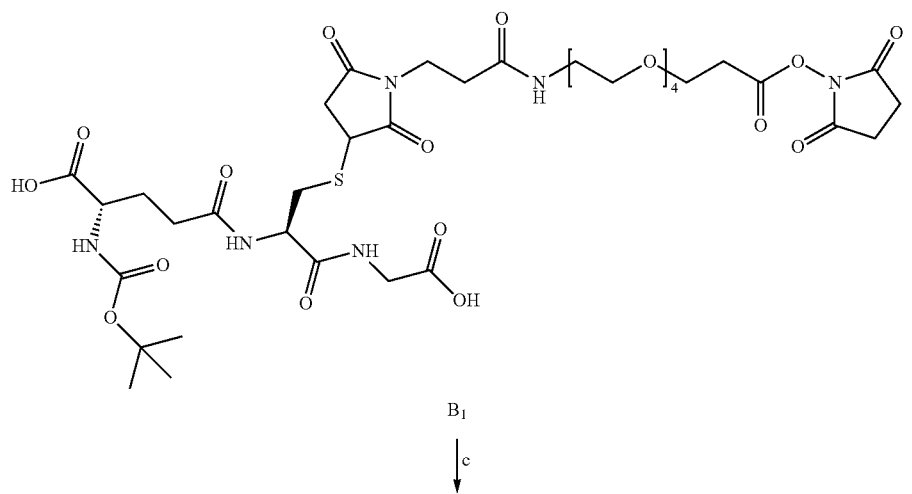
$B_1$
↓ c

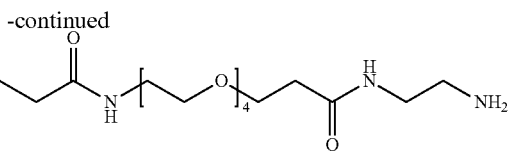
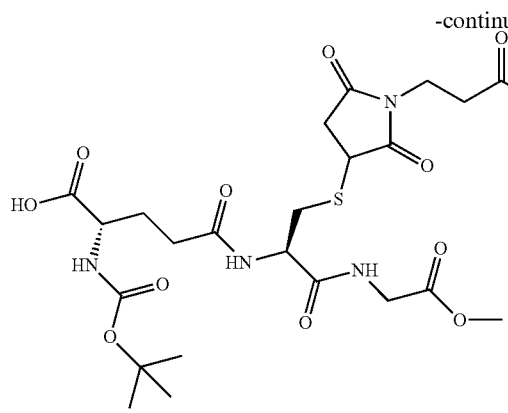

B a Boc₂O, THF/H₂O;
b 1) TCEP, H₂O, 2) Mal-PEG₄-NHS, H₂O/MeOH;
c ethylenediamine MeOH (1) Compound $B_0$
(2S,2'S)-5,5'-(((2R,2'R)-disulfanediylbis(1-((carboxymethyl)amino)-1-oxopropan-3,2-diyl))bis(azanediyl))bis(2-amino-5-oxopentanoic) acid, Compound $B_0$: 150 mg of oxidized glutathione (0.24 mmol, 1.0 eq) was dissolved in 3 ml of water and 111 mg of Boc-anhydride (0.50 mmol, 2.05 eq) dissolved in 3 ml of methanol wad added to the solution. To provide basic pH, DIEA was added to the reaction mixture. After 12 hours, all substances were evaporated and the crude product was used without further purification in the next step. Analytical HPLC showed 99% purity ($R_T$=16.5 min). HRMS (ESI−) m/z for $C_{30}H_{48}O_{16}N_6S_2$[M-H]⁻: calculated: 811, 24954, found 811, 24991.

(2) Compound $B_1$
(6S,6'S,11R,11'R)-11,11'-(disulfanediylbis(methylen))bis(6-carboxy-2,2-dimethyl-4,9,12-trioxo-3-oxa-5,10,13-triazapentadecane-15-oic) acid, Compound $B_1$: 90 mg of Compound $B_0$ (0.11 mmol, 1.0 eq) was dissolved in 1 ml of water and the solution was purged with nitrogen under stirring for 10 min. 35 mg of tris(2-carboxyethyl) phosphine (TCEP; 0.12 mmol, 1.1 eq) was added and the reaction was stirred for 2 h under inert atmosphere. HPLC analysis proved complete disappearance of Compound $B_0$. Then, 114 mg of mal-dPEG₄-NHS (0.22 mmol, 2.0 eq, #PEG1575.0001, IRIS Biotech GmbH) dissolved in 1 ml of methanol was added. After 3 hours the volatiles were evaporated and the crude product was purified by preparative HPLC (gradient of 15-50% ACN in 50 min, $R_T$=32 min). After lyophilization, 95 mg of Compound $B_1$ was isolated (yield 47%). Analytical HPLC: $R_T$=16.8. HRMS (ESI−) m/z for $C_{37}H_{56}O_{19}N_6S$ [M-H]⁻ calculated 919.32482. found 919.32444.

(3) Compound B
46 mg of Compound $B_1$ (50 μmol, 1.0 eq) was dissolved in 1 ml of methanol, and 20 μl of freshly redistilled ethylenediamine (300 μmol, 6.0 eq) was added to the reaction mixture. The reaction mixture was allowed to react under stirring for 3 hours. The volatiles were evaporated and the product was purified by preparative HPLC (gradient of 15-40% ACN in 50 min, $R_T$=29 min). After lyophilization, 43 mg of Compound B was isolated (yield 46%). Analytical HPLC: $R_T$=14.7. HRMS (ESI−) m/z for $C_{45}H_{58}O_{16}N_7S$ [M-H]⁻: calculated 866.38143. found 866.38118.

Example 9: Preparation of Conjugate 5

The polymeric precursor poly (HPMA-co-Ma-β-Ala-TT) (0.040 g, $M_w$=81600 g/mol, 14.6 mol % TT; see Preparation of Conjugate 1), Compound B (5.5 mg) and N-(2-aminoethyl) biotinamid hydrobromide (biotin-NH₂) (5 mg) were dissolved in 0.2 ml of DMSO. ATTO488-NH₂ (2.5 mg) was dissolved in 0.1 ml of DMSO and added to a solution of the polymeric precursor. Then, N,N-diisopropylethylamine (DIPEA) (8.0 μl) was added and the reaction mixture was stirred for 4 hours at room temperature. Subsequently, 1-aminopropan-2-ol (5 μl) was added to the solution and the reaction mixture was stirred for 10 min. Then, the polymeric conjugate 5 poly(HPMA-co-Ma-β-Ala-CompoundB-co-Ma-β-Ala-ATTO488-co-Ma-β-Ala-NH-biotin) was isolated by precipitation in acetone:diethyl ether (3:1), filtered, washed with acetone and diethyl ether and dried in vacuum. Polymeric conjugate was purified from low-molecular impurities by column chromatography on Sephadex LH-20 in methanol, precipitated in diethyl ether, filtered and dried in vacuum. The yield of the Conjugate 5 was 20 mg. Content of ATTO488 4.78% was determined spectrophotometrically ($\varepsilon_{502nm}$=90000 l·mol⁻¹·cm⁻¹, distilled water) and the glutathione content 10.87% was determined in sample hydrolyzate (6N—HCl, 115° C., 16 hr) by HPLC with fluorescence detector (Ex. 229 nm, Em. 450 nm), column: Chromolith C18, precolumn derivatisation method with o-phthaldialdehyde.

Example 10: Preparation of Conjugate 6

The polymeric precursor poly(HPMA-co-Ma-β-Ala-TT) (0.030 mg, $M_w$=81600 g/mol, 14.6 mol % TT; see Preparation of Conjugate 1), Compound B (3.8 mg) and N-(2-aminoethyl) biotinamid hydrobromide (biotin-NH₂) (4 mg) were dissolved in 0.3 ml of DMSO. N,N-diisopropylethylamine (DIPEA) (4.0 μl) was added, the reaction mixture was stirred for 4 hours at room temperature and then 1-aminopropan-2-ol (2 μl) was added to the solution and the reaction mixture was stirred for 10 min. Then, the polymeric conjugate 6 poly(HPMA-co-Ma-β-Ala-CompoundB-co-Ma-β-Ala-NH-biotin) was isolated by precipitation into acetone: diethyl ether (3:1), filtered, washed with acetone and diethyl ether and dried in vacuum. Polymeric conjugate was purified from low-molecular impurities by column chromatography on Sephadex LH-20 in methanol, precipitated in diethyl ether, filtered and dried in vacuum. The yield of Conjugate 6 was 18 mg. Biotin content 5.23% was determined using the HABA/Avidin kit (Sigma) and glutathione content 10.85% was determined in the sample hydrolysate (6N—HCl, 115° C., 16 hours) by HPLC with fluorescence detector (Ex. 229 nm, Em. 450 nm), column: Chromolith C18, precolumn derivatisation method with o-phthaldialdehyde.

Example 11: Affinity Isolation ("Pull-Down") of Recombinant Human Protein GCPII with GST Affinity Tag (GST-rhGCPII) Using Conjugate 5 and Conjugate 6

Affinity isolation of GST-rhGCPII was conducted analogously as the isolation of the protein labeled the His-tag (see Example 5).

Conjugate 5, Conjugate 6, Conjugate 3 and Conjugate 4 were pre-bound to 20 µl of Streptavidin Sepharose (200 nM solution in 1000 µl of TBST, 1 hr, 6° C.). After washing with 3×1000 µl TBST, the resin was mixed with 1000 µl of a solution of GST-rhGCPII (5 ng/µl in TBST or lysate of LNCaP cells) and incubated at 6° C. for 3 hours. The resin was then washed with 3×1000 µl TBST and subsequently, proteins were eluted by addition of 50 µl of sample buffer for SDS-PAGE and by heating to 98° C. for 10 min.

GST-rhGCPII protein was successfully isolated with Conjugate 5 and Conjugate 6 from both samples (both from pure buffer, and from the lysate of LNCaP cells). Each of the negative controls (conjugate without inhibitor and conjugate without inhibitor and ATTO488) showed that the binding of GST-rhGCPII happens specifically via a binding group present on the conjugate.

Example 12: Quantification of the Interactions of Polymeric Conjugates with the GST-rhGCPII Using Surface Plasmon Resonance (SPR)

Measuring the interaction of GST-rhGCPII with Conjugates 5 and 6 using surface plasmon resonance (SPR) was performed on a four-channel SPR sensor developed at the Institute of Photonics and Electronics AS CR in Prague [10-11]. In a typical experiment, the SPR chip (supplied by IPE ASCR) immersed in ethanol solution (7:3) of alkanethiols HS—$(CH_2)_{11}$-$PEG_4$-OH and HS—$(CH_2)_{11}$-$PEG_6$-O—$CH_2$—COOH (Prochimia) at a final concentration of 0.2 mM for 1 h at 37° C. The chip was subsequently rinsed with ethanol for UV spectroscopy, with deionized water and dried with nitrogen. Finally, the chip is attached to a SPR chip prism; all measurements were performed at 25° C.

Activation of the terminal carboxyl groups on the sensor surface was carried out in situ by addition of a mixture (1:1) 11.51 mg/ml N-hydroxysuccinimide (NHS, Biacore), and 76.68 mg/ml 1-ethyl-3-(3-dimethylaminopropyl)-carbodiimide hydrochloride (EDC, Biacore) in deionized water for 5 min at 20 µl/min. Following steps of the experiment were then conducted at a flow rate of 30 µl/min. Subsequently, neutravidin solution (20 ng/µl) in 10 mM sodium acetate, pH 5.0 was applied for 8 min. To remove non-specifically bound molecules of neutravidin, buffer of high ionic strength (PBS with 0.5 M NaCl) was used, and then for deactivation of the remaining activated carboxyl groups, 1 M ethanolamine (Biacore) was applied. Conjugate of 5 or 6 (1 µM in TBS, for 10 min) was then bound to immobilized neutravidin. Finally, a solution of recombinant protein GST-rhGCPII in TBS in varying concentrations was injected on this prepared layer (the concentrations of GST-rhGCPII were 100, 200, 400 and 800 nM) and subsequently only TBS (dissociation phase). Curves describing the bond were exported and analyzed in TraceDrawer v.1.5 (Ridgeview Instruments AB) to obtain the parameters $k_{on}$ a $k_{off}$.

The value of the dissociation constant between the GST-rhGCPII and Conjugate 5 was determined $K_D$=12 nM; between GST-rhGCPII and Conjugate 6 $K_D$=9 nM.

Example 13: Immobilization of GST-rhGCPII and Subsequent Testing of the Inhibitory Potency of GCPII Inhibitors The experiment was performed analogously to the experiment with immobilization of GCPII via His-tag (Example 7).

10 µl solution of streptavidin (10 ug/µl) in 100 mM borate buffer, pH 9.5, was applied to the bottom of wells in a 96 well FrameStar 480/96 plate and incubated at room temperature for 1 hour. The contents of wells was then tapped out and wells were washed three times with 200 µl of TBS. Unoccupied surface of the wells was blocked with 0.55% (w/v) solution of casein in TBS (Casein Buffer 20×-4× Concentrate, SDT, 24 h). After further washing with 3×200 µl TBST, Conjugate 6 or 4 (100 nM in TBST, 2 hrs) was bound to streptavidin. Unbound conjugates were washed away by washing with 3×200 µl of TBST and a solution of recombinant GST-rhGCPII in TBST (10 ng/well, 1 hr, prepared according to [9]) was subsequently added to the wells. After washing with 3×200 µl of TBST, either detection probe ssPSMA alone (1 nM in TBST) binding to the active site of GST-rhGCPII, or a mixture of this probe and a selected test substance in a selected concentration (typically 100 µM in TBST) were added. After incubation for 1 hr at room temperature, the wells were washed 5×200 µl of TBST and the amount of bound detection probe was then determined by qPCR. From the changes in the amount of bound probe in wells incubated with test compound compared to wells incubated with the probe alone, the fraction of active sites of the GST-rhGCPII occupied by a given test substance was calculated, and consequently the inhibition constant of the substance (a detailed description of the ssPSMA detection probe and a method to calculate the inhibition constants are given in Czech patent application PV 2014-527).

With this method, it was possible to determine the inhibition constant of the tested inhibitor by measuring the sample in a single well; this method was used to measure twenty inhibitors and $K_i$ values obtained corresponded to the $K_i$ values acquired by measuring GST-rhGCPII enzyme kinetics.

Conjugates 5 and 6 containing a binding group for the GST-tag were used for the affinity isolation and purification of proteins with GST-tag from various samples. Bond between these polymers and the protein carrying the GST-tag was analyzed by SPR; dissociation constant of the binding was in the nanomolar range (about 10 nM). Further, in an analogous way as for the conjugate binding His-tag, the conjugate was used for the immobilization of proteins with GST-tag and subsequent testing of substances competing for binding with a known ligand of the protein.

REFERENCES

1. Ulbrich, K. and V. Subr, *Structural and chemical aspects of HPMA copolymers as drug carriers*. Adv Drug Deliv Rev, 2010. 62(2): p. 150-66.
2. Ulbrich, K., et al., *Polymeric drugs based on conjugates of synthetic and natural macromolecules I. Synthesis and* physico-chemical characterisation. Journal of Controlled Release, 2000. 64(1-3): p. 63-79.
3. Etrych, T., et al., *N-(2-hydroxypropyl)methacrylamide-based polymer conjugates with pH-controlled activation of doxorubicin. I. New synthesis, physicochemical characterization and preliminary biological evaluation.* Journal of Applied Polymer Science, 2008. 109(5): p. 3050-3061.
4. Subr, V., et al., *Synthesis of Well-Defined Semitelechelic Poly[N-(2-hydroxypropyl)methacrylamide] Polymers with Functional Group at the alpha-End of the Polymer Chain by RAFT Polymerization.* Macromolecules, 2013. 46(6): p. 2100-2108.
5. Subr, V. and K. Ulbrich, *Synthesis and properties of new N-(2-hydroxypropyl)-methacrylamide copolymers containing thiazolidine-2-thione reactive groups.* Reactive & Functional Polymers, 2006. 66(12): p. 1525-1538.
6. Kopecek, J., P. Rejmanova, and V. Chytry, *Polymers Containing Enzymatically Degradable Bonds 0.1. Chymotrypsin Catalyzed-Hydrolysis of Para-Nitroanilides of Phenylalanine and Tyrosine Attached to Side-Chains of Co-Polymers of N-(2-Hydroxypropyl)Methacrylamide.* Makromolekulare Chemie-Macromolecular Chemistry and Physics, 1981. 182(3): p. 799-809.
7. Huang, Z., et al., *Tris-nitrilotriacetic acids of subnanomolar affinity toward hexahistidine tagged molecules.* Bioconjug Chem, 2009. 20(8): p. 1667-72.
8. Perrier, S., P. Takolpuckdee, and C. A. Mars, *Reversible addition-fragmentation chain transfer polymerization: End group modification for functionalized polymers and chain transfer agent recovery.* Macromolecules, 2005. 38(6): p. 2033-2036.
9. Tykvart, J., et al., *Efficient and versatile one-step affinity purification of in vivo biotinylated proteins: expression, characterization and structure analysis of recombinant human glutamate carboxypeptidase II.* Protein Expr Purif, 2012. 82(1): p. 106-15.
10. Hegnerova, K., et al., *Surface plasmon resonance biosensors for detection of Alzheimer disease biomarker.* Sensors and Actuators B-Chemical, 2009. 139(1): p. 69-73.
11. Pimkova, K., et al., *Surface plasmon resonance biosensor for the detection of VEGFR-1-a protein marker of myelodysplastic syndromes.* Analytical and Bioanalytical Chemistry, 2012. 402(1): p. 381-387.

The invention claimed is:

1. Synthetic macromolecular conjugate for selective interaction with proteins, characterized in that it comprises a synthetic copolymer, and at least one binding group and at least one further group selected from an affinity tag and an imaging probe, said at least one binding group and at least one further group being bound via covalent bond to said synthetic copolymer,
wherein
the synthetic copolymer is a copolymer obtainable by copolymerization of at least one monomer of Formula 1:

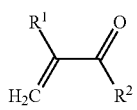

(1)

wherein:
R$^1$ is selected from H, CH$_3$; and
R$^2$ is selected from NH$_2$, NH—CH$_2$—CH(OH)—CH$_3$, NH—CH$_3$, NH—CH$_2$CH$_3$, NH—CH$_2$CH$_2$—OH, NH—CH$_2$CH$_2$CH$_2$—OH, NHC(CH$_2$OH)$_3$, NH—CH$_2$CH$_2$—N$^+$(CH$_3$)$_3$Cl$^-$, O—CH$_2$CH$_2$—OH, O—(CH$_2$CH$_2$O)$_2$—H, O—(CH$_2$CH$_2$O)$_3$—H, O—CH$_2$CH$_2$—N$^+$(CH$_3$)$_3$Cl$^-$, NH—(CH$_2$)$_3$N$^+$(CH$_3$)$_2$—(CH$_2$)$_2$—COO$^-$;

and at least one monomer of Formula 2:

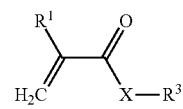

(2)

wherein:
R$^1$ is selected from H, CH$_3$; and
X is selected from NH—(CH$_2$)$_2$—CO, NH—(CH$_2$)$_3$—CO, NH—(CH$_2$)$_4$—CO, NH—(CH$_2$)$_5$—CO, Gly, GlyGly, GlyPheLeuGly; and
R$^3$ is selected from:

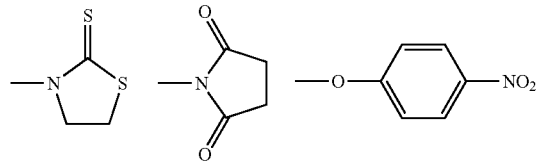

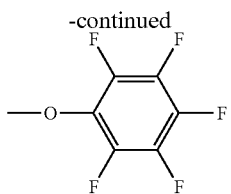

whereas in the copolymer at least one reactive group $R^3$ is replaced by the binding group, at least one reactive group $R^3$ is replaced by the affinity tag and/or at least one reactive group $R^3$ is replaced by the imaging probe, and wherein the binding group is selected from nitrilotriacetic acid and tris(nitriloacetic) acid.

2. The macromolecular conjugate according to claim 1, characterized in that the molecular weight of the conjugate is in the range of 1000 to 500000 g/mol, preferably in the range from 20000 to 150000 g/mol.

3. The macromolecular conjugate according to claim 1, characterized in that the binding group is bound to the synthetic copolymer via a flexible linker, preferably via a linker based on polyethylene glycol, peptide, preferably a peptide having a molecular weight in the range of 100 to 5000 g/mol, or nucleic acid, preferably a nucleic acid containing 1 to 40 nucleotides, or oligosaccharide, preferably an oligosaccharide containing 1 to 40 monosaccharides.

4. The macromolecular conjugate according to claim 1, characterized in that the affinity tag is present and it is selected from the group comprising biotin, FLAG tag, His-tag, HA tag, Strep-tag, Avi-tag, GST, c-myc-tag, V5-tag, E-tag, S-tag, SBP-tag, poly(Glu)-taq, and calmodulin.

5. The macromolecular conjugate according to claim 1, characterized in that the imaging probe is present and is selected from the group comprising fluorescent moieties, radionuclides and metal complexes.

6. The macromolecular conjugate according to claim 5, characterized in that the imaging probe is selected from the group comprising fluorophores with an excitation maximum in the range of 350 to 850 nm, preferably ATTO488 or DY676; lanthanide complexes, preferably of Gd, Mn, Dy, Eu; radionuclide complexes $^{64}Cu$, $^{68}Ga$, $^{18}F$, $^{99m}TC$, $^{123}I$, $^{125}I$, $^{131}I$, $^{57}Co$, $^{51}Cr$, $^{67}Ga$, $^{64}Cu$, $^{111}In$, $^{90}Y$.

7. A Method of identification, visualization, quantification or isolation of proteins, comprising the steps of:
providing a synthetic macromolecular conjugate for selective interaction with proteins, characterized in that it comprises a synthetic copolymer, and at least one binding group and at least one further group selected from an affinity tag and an imaging probe, said at least one binding group and at least one further group being bound via covalent bond to said synthetic copolymer, wherein
the synthetic copolymer is a copolymer obtainable by copolymerization of at least one monomer of Formula 1:

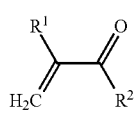

wherein:
$R^1$ is selected from H, $CH_3$; and
$R^2$ is selected from $NH_2$, $NH$—$CH_2$—$CH(OH)$—$CH_3$, $NH$—$CH_3$, $NH$—$CH_2CH_3$, $NH$—$CH_2CH_2$—$OH$, $NH$—$CH_2CH_2CH_2$—$OH$, $NHC(CH_2OH)_3$, $NH$—$CH_2CH_2$—$N^+(CH_2)_2Cl^-$, $O$—$CH_2CH_2$—$OH$, $O$—$(CH_2CH_2O)_2$—$H$, $O$—$(CH_2CH_2O)_3$—$H$, $O$—$CH_2CH_2$—$N^+(CH_3)_3Cl^-$, $NH$—$(CH_2)_3N^+(CH_3)_2$—$(CH_2)_2$—$COO^-$;

and at least one monomer of Formula 2:

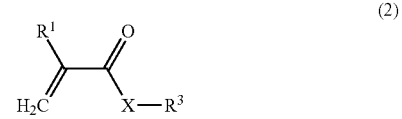

wherein:
$R^1$ is selected from H, $CH_3$; and
X is selected from NH—$(CH_2)_2$—CO, NH—$(CH_2)_3$—CO, NH—$(CH_2)_4$—CO, NH—$(CH_2)_5$—CO, Gly, GlyGly, GlyPheLeuGly; and
$R^3$ is selected from:

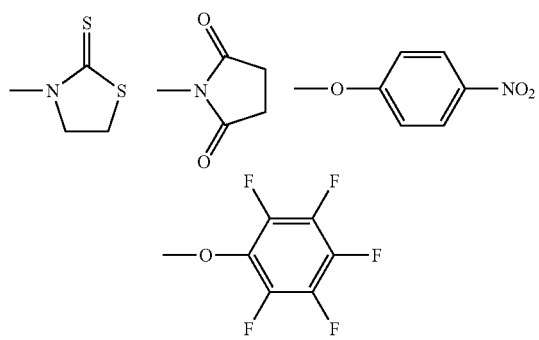

whereas in the copolymer at least one reactive group $R^3$ is replaced by the binding group, at least one reactive group $R^3$ is replaced by the affinity tag and/or at least one reactive group $R^3$ is replaced by the imaging probe, and wherein the binding group is selected from nitrilotriacetic acid and tris(nitriloacetic) acid;

binding the macromolecular conjugate to a target protein; and performing a step of identification, visualization, quantification or isolation of the target protein using the affinity tag and/or the imaging probe.

8. An immunochemical method, comprising the steps of:
providing a synthetic macromolecular conjugate for selective interaction with proteins, characterized in that it comprises a synthetic copolymer, and at least one binding group and at least one further group selected from an affinity tag and an imaging probe, said at least one binding group and at least one further group being bound via covalent bond to said synthetic copolymer, wherein
the synthetic copolymer is a copolymer obtainable by copolymerization of at least one monomer of Formula 1:

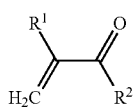

wherein:
R$^1$ is selected from H, CH$_3$; and
R$^2$ is selected from NH$_2$, NH—CH$_2$—CH(OH)—CH$_3$, NH—CH$_3$, NH—CH$_2$CH$_3$, NH—CH$_2$CH$_2$—OH, NH—CH$_2$CH$_2$CH$_2$—OH, NHC(CH$_2$OH)$_3$, NH—CH$_2$CH$_2$—N$^+$(CH$_2$)$_2$Cl$^-$, O—CH$_2$CH$_2$—OH, O—(CH$_2$CH$_2$O)$_2$—H, O—(CH$_2$CH$_2$O)$_3$—H, O—CH$_2$CH$_2$—N$^+$(CH$_3$)$_3$Cl$^-$, NH—(CH$_2$)$_3$N$^+$(CH$_3$)$_2$—(CH$_2$)$_2$—COO$^-$;
and at least one monomer of Formula 2:

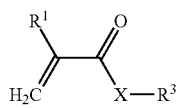

wherein:
R$^1$ is selected from H, CH$_3$; and
X is selected from NH—(CH$_2$)$_2$—CO, NH—(CH$_2$)$_3$—CO, NH—(CH$_2$)$_4$—CO, NH—(CH$_2$)$_5$—CO, Gly, GlyGly, GlyPheLeuGly; and
R$^3$ is selected from:

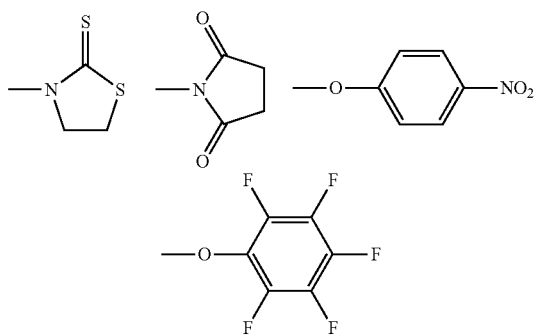

whereas in the copolymer at least one reactive group R$^3$ is replaced by the binding group, at least one reactive group R$^3$ is replaced by the affinity tag and/or at least one reactive group R$^3$ is replaced by the imaging probe, and wherein the binding group is selected from nitrilotriacetic acid and tris(nitriloacetic) acid;

binding the macromolecular conjugate to a target protein; and performing a detection step using the affinity tag and/or the imaging probe.

9. A method of screening of inhibitors, ligands, and compounds and substances capable of binding to a target protein, comprising the steps of:
providing a synthetic macromolecular conjugate for selective interaction with proteins, characterized in that it comprises a synthetic copolymer, and at least one binding group and at least one further group selected from an affinity tag and an imaging probe, said at least one binding group and at least one further group being bound via covalent bond to said synthetic copolymer, wherein
the synthetic copolymer is a copolymer obtainable by copolymerization of at least one monomer of Formula 1:

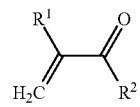

wherein:
R$^1$ is selected from H, CH$_3$; and
R$^2$ is selected from NH$_2$, NH—CH$_2$—CH(OH)—CH$_3$, NH—CH$_3$, NH—CH$_2$CH$_3$, NH—CH$_2$CH$_2$—OH, NH—CH$_2$CH$_2$CH$_2$—OH, NHC(CH$_2$OH)$_3$, NH—CH$_2$CH$_2$—N$^+$(CH$_2$)$_2$Cl$^-$, O—CH$_2$CH$_2$—OH, O—(CH$_2$CH$_2$O)$_2$—H, O—(CH$_2$CH$_2$O)$_3$—H, O—CH$_2$CH$_2$—N$^+$(CH$_3$)$_3$Cl$^-$, NH—(CH$_2$)$_3$N$^+$(CH$_3$)$_2$—(CH$_2$)$_2$—COO$^-$;
and at least one monomer of Formula 2:

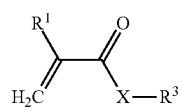

wherein:
R$^1$ is selected from H, CH$_3$; and
X is selected from NH—(CH$_2$)$_2$—CO, NH—(CH$_2$)$_3$—CO, NH—(CH$_2$)$_4$—CO, NH—(CH$_2$)$_5$—CO, Gly, GlyGly, GlyPheLeuGly; and
R$^3$ is selected from:

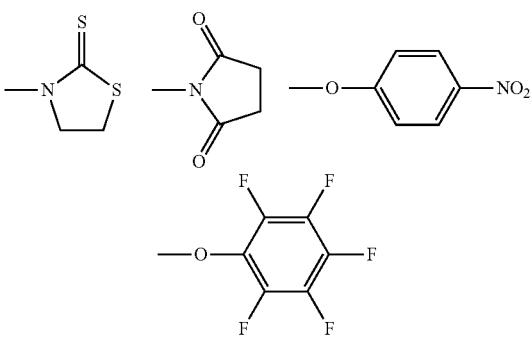

whereas in the copolymer at least one reactive group R$^3$ is replaced by the binding group, at least one reactive group R$^3$ is replaced by the affinity tag and/or at least one reactive group R$^3$ is replaced by the imaging probe, and wherein the binding group is selected from nitrilotriacetic acid and tris(nitriloacetic) acid;

performing a step of immobilization of a target protein by binding the macromolecular conjugate to the target protein.

10. The immunochemical method according to claim 8, wherein the immunochemical method is selected from the group consisting of ELISA, Wester blotting and modifications thereof, flow cytometry, immunoprecipitation, and immunocytochemistry.

\* \* \* \* \*